(12) United States Patent
Kramer et al.

(10) Patent No.: US 6,285,907 B1
(45) Date of Patent: Sep. 4, 2001

(54) SYSTEM PROVIDING VENTRICULAR PACING AND BIVENTRICULAR COORDINATION

(75) Inventors: Andrew P. Kramer, Stillwater; Jeffrey E. Stahmann, Ramsey; Rene H. Wentkowski, White Bear Lake; Kenneth L. Baker, Shoreview; Jesse W. Hartley, Lino Lakes; David B. Krig, Brooklyn Park, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/316,588

(22) Filed: May 21, 1999

(51) Int. Cl.$^7$ ................................................ A61N 1/365
(52) U.S. Cl. ................................................ 607/9; 607/25
(58) Field of Search .................................... 607/9, 17, 25

(56) References Cited

U.S. PATENT DOCUMENTS

| | | | |
|---|---|---|---|
| 3,857,399 | 12/1974 | Zacouto | 128/419 |
| 4,030,510 | 6/1977 | Bowers | 128/419 PG |
| 4,163,451 | 8/1979 | Lesnick et al. | 128/419 PG |
| 4,556,063 | 12/1985 | Thompson et al. | 128/419 PT |
| 4,830,006 | 5/1989 | Haluska et al. | 128/419 PG |
| 4,917,115 | 4/1990 | Flammang et al. | 128/419 PG |
| 4,920,965 | 5/1990 | Funke et al. | 128/419 PG |
| 4,928,688 | 5/1990 | Mower | 128/419 PG |
| 4,998,974 | 3/1991 | Aker | 128/419 PG |
| 5,085,215 | 2/1992 | Nappholz et al. | 128/419 PG |
| 5,127,404 | 7/1992 | Wyborny et al. | 128/419 P |
| 5,129,394 | 7/1992 | Mehra | 128/419 PG |
| 5,139,020 | 8/1992 | Koestner et al. | 128/419 PG |
| 5,156,154 | 10/1992 | Valenta, Jr. et al. | 128/661.09 |
| 5,183,040 | 2/1993 | Nappholz et al. | 128/419 PG |
| 5,188,106 | 2/1993 | Nappholz et al. | 128/419 PG |
| 5,207,219 | 5/1993 | Adams et al. | 128/419 D |
| 5,282,836 | 2/1994 | Kreyenhagen et al. | 607/4 |
| 5,284,491 | 2/1994 | Sutton et al. | 607/17 |
| 5,292,339 | 3/1994 | Stephens et al. | 607/15 |
| 5,312,452 | 5/1994 | Salo | 607/17 |

(List continued on next page.)

FOREIGN PATENT DOCUMENTS

| | | | |
|---|---|---|---|
| 0033418 | 12/1980 | (EP) | A61N/1/36 |
| 97/11745 | 4/1997 | (WO) | A61N/1/362 |
| 98/48891 | 11/1998 | (WO) | A61N/1/362 |

OTHER PUBLICATIONS

*Harmony, Automatic Dual Chamber Pacemaker, Product Information and Programming Guide*, Viatron Medical, 22 p., (Date Unknown), Harmony Dual Chamber mentioned in publication and Clinica, 467, p. 16, Sep. 11, 1991, "Rate Devices Impact Pacemaker Market", Clinica , 417, p. 9, Sep. 5, 1990, "French CNH Equipment Approvals".

(List continued on next page.)

*Primary Examiner*—Jeffrey R. Jastrzab
(74) *Attorney, Agent, or Firm*—Schwegman, Lundberg, Woessner & Kluth, P.A.

(57) ABSTRACT

A cardiac rhythm management system includes techniques for computing an indicated pacing interval, AV delay, or other timing interval. In one embodiment, a variable indicated pacing interval is computed based at least in part on an underlying intrinsic heart rate. The indicated pacing interval is used to time the delivery of biventricular coordination therapy even when ventricular heart rates are irregular, such as in the presence of atrial fibrillation. In another embodiment, a variable filter indicated AV interval is computed based at least in part on an underlying intrinsic AV interval. The indicated AV interval is used to time the delivery of atrial tracking biventricular coordination therapy when atrial heart rhythms are not arrhythmic. Other indicated timing intervals may be similarly determined. The indicated pacing interval, AV delay, or other timing interval can also be used in combination with a sensor indicated rate indicator.

71 Claims, 18 Drawing Sheets

U.S. PATENT DOCUMENTS

| | | | |
|---|---|---|---|
| 5,331,966 | 7/1994 | Bennett et al. | 128/696 |
| 5,350,409 | 9/1994 | Stoop et al. | 607/17 |
| 5,365,932 | 11/1994 | Greenhut | 128/696 |
| 5,383,910 | 1/1995 | den Dulk | 607/14 |
| 5,391,189 | 2/1995 | van Krieken et al. | 607/17 |
| 5,395,397 | 3/1995 | Lindgren et al. | 607/9 |
| 5,400,796 | 3/1995 | Wecke | 128/705 |
| 5,411,524 | 5/1995 | Rahul | 607/4 |
| 5,411,531 | 5/1995 | Hill et al. | 607/14 |
| 5,417,714 | 5/1995 | Levine et al. | 607/9 |
| 5,462,060 | 10/1995 | Jacobson et al. | 128/702 |
| 5,480,413 | 1/1996 | Greenhut et al. | 604/14 |
| 5,486,198 | 1/1996 | Ayers et al. | 607/5 |
| 5,487,752 | 1/1996 | Salo et al. | 607/17 |
| 5,507,782 | 4/1996 | Kieval et al. | 607/9 |
| 5,507,784 | 4/1996 | Hill et al. | 607/14 |
| 5,514,163 | 5/1996 | Markowitz et al. | 607/9 |
| 5,522,859 | 6/1996 | Stroebel et al. | 607/19 |
| 5,527,347 | 6/1996 | Shelton et al. | 607/9 |
| 5,534,016 | 7/1996 | Boute | 607/9 |
| 5,540,727 | 7/1996 | Tockman et al. | 607/18 |
| 5,545,186 | 8/1996 | Olson et al. | 607/14 |
| 5,560,369 | 10/1996 | McClure et al. | 128/704 |
| 5,584,864 | 12/1996 | White | 607/5 |
| 5,584,867 | 12/1996 | Limousin et al. | 607/9 |
| 5,626,620 | 5/1997 | Kieval et al. | 607/9 |
| 5,626,623 | 5/1997 | Kieval et al. | 607/23 |
| 5,632,267 | 5/1997 | Högnelid et al. | 607/5 |
| 5,674,255 | 10/1997 | Walmsley et al. | 607/14 |
| 5,690,689 | 11/1997 | Sholder | 607/24 |
| 5,700,283 | 12/1997 | Salo | 607/17 |
| 5,713,929 | 2/1998 | Hess et al. | 607/14 |
| 5,713,932 | 2/1998 | Gillberg et al. | 607/27 |
| 5,716,383 | 2/1998 | Kieval et al. | 607/9 |
| 5,725,561 | 3/1998 | Stroebel et al. | 607/4 |
| 5,730,141 | 3/1998 | Fain et al. | 128/705 |
| 5,730,142 | 3/1998 | Sun et al. | 128/705 |
| 5,738,096 | 4/1998 | Ben-Haim | 128/653.1 |
| 5,741,308 | 4/1998 | Sholder | 607/9 |
| 5,749,906 | 5/1998 | Kieval et al. | 607/9 |
| 5,755,736 | 5/1998 | Gillberg et al. | 607/4 |
| 5,755,737 | 5/1998 | Prieve et al. | 607/4 |
| 5,776,164 | 7/1998 | Ripart | 607/5 |
| 5,776,167 | 7/1998 | Levine et al. | 607/9 |
| 5,788,717 | 8/1998 | Mann et al. | 607/14 |
| 5,800,464 | 9/1998 | Kieval | 607/9 |
| 5,800,471 | 9/1998 | Baumann | 607/25 |
| 5,814,077 | 9/1998 | Sholder et al. | 607/9 |
| 5,814,085 | 9/1998 | Hill | 607/14 |
| 5,836,975 | 11/1998 | DeGroot | 607/5 |
| 5,836,987 | 11/1998 | Baumann et al. | 607/17 |
| 5,846,263 | 12/1998 | Peterson et al. | 607/14 |
| 5,855,593 | 1/1999 | Olson et al. | 607/9 |
| 5,861,007 | 1/1999 | Hess et al. | 607/9 |
| 5,873,895 | 2/1999 | Sholder et al. | 607/9 |
| 5,873,897 | 2/1999 | Armstrong et al. | 607/14 |
| 5,893,882 | 4/1999 | Peterson et al. | 607/14 |
| 5,897,575 | 4/1999 | Wickham | 607/4 |
| 5,928,271 | 7/1999 | Hess et al. | 607/14 |
| 5,931,857 | 8/1999 | Prieve et al. | 607/14 |
| 5,935,081 | 8/1999 | Kadhiresan | 600/513 |
| 5,944,744 | 8/1999 | Paul et al. | 607/9 |
| 5,951,592 | 9/1999 | Murphy | 607/4 |
| 5,978,707 | 11/1999 | Krig et al. | 607/14 |
| 5,978,710 | 11/1999 | Prutchi et al. | 607/17 |
| 5,983,138 | 11/1999 | Kramer | 607/9 |
| 5,987,356 | 11/1999 | DeGroot | 607/5 |
| 5,991,656 | 11/1999 | Olson et al. | 607/4 |
| 5,999,850 | 12/1999 | Dawson et al. | 607/4 |
| 6,026,320 | 2/2000 | Carlson et al. | 600/510 |
| 6,044,298 | 3/2000 | Salo et al. | 607/17 |
| 6,049,735 | 4/2000 | Hartley et al. | 607/9 |
| 6,052,620 | 4/2000 | Gillberg et al. | 607/4 |
| 6,081,745 | 6/2000 | Mehra | 607/4 |

OTHER PUBLICATIONS

*Metrix Model 3020 Implantable Atrial Defibrillator*, Physician's Manual, InControl, Inc., Redmond, WA, Redmond, WA, pp. 4–24–4–27, (1998).

Ayers, G.M., et al., "Ventricular Proarrhythmic Effects of Ventricular Cycle Length and Shock Strength in a Sheep model of Transvenous Atrial Defibrillation", *Circulation*, 89 (1), pp. 413–422, (Jan. 1994).

Duckers, H.J., et al., "Effective use of a novel rate–smoothing algorithm in atrial fibrillation by ventricular pacing", *European Heart Journal*, 18, pp. 1951–1955, (1997).

Fahy, G.J., et al., "Pacing Strategies to Prevent Atrial Fibrillation", *Atrial Fibrillation*, 14 (4), pp. 591–596, (Nov. 1996).

Greenhut, S., et al., "Effectiveness of a Ventricular Rate Stabilization Algorithm During Atrial Fibrillation in Dogs", *Pace*, Abstract, 1 p., (1996).

Heuer, H., et al., "Dynamic Dual–Chamber Overdrive Pacing with an Implantable Pacemaker System: A New Method for Terminating Slow Ventricular Tachycardia", *Zeitschrift fur Kardiologie*, 75, German Translation by the Ralph McElroy Translation Company, Austin, TX, 5 p., (1986).

Wittkampf, F., et al., "Rate Stabilization by Right Ventricular Pacing in Patients with Atrial Fibrillation", *Pace*, 9, pp. 1147–1153, (1986).

SYSTEM PROVIDING VENTRICULAR PACING AND BIVENTRICULAR COORDINATION

CROSS REFERENCE TO RELATED APPLICATIONS

This application is related to the following co-pending, commonly assigned patent applications: "Method and Apparatus for Treating Irregular Ventricular Contractions Such as During Atrial Arrhythmia," U.S. Ser. No. 09/316,515, "Cardiac Rhythm Management System Promoting Atrial Pacing," U.S. Ser. No. 09/316,682, and "Cardiac Rhythm Management System With Atrial Shock Timing Optimization," U.S. Ser. No. 09/316,741, each of which are filed on even date herewith, each of which disclosure is herein incorporated by reference in its entirety.

TECHNICAL FIELD

The present system relates generally to cardiac rhythm management systems and particularly, but not by way of limitation, to a system providing, among other things, ventricular pacing and biventricular coordination therapy.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is the treatment of congestive heart failure (also referred to as "CHF"). Congestive heart failure, which can result from long-term hypertension, is a condition in which the muscle in the walls of at least one of the right and left sides of the heart deteriorates. By way of example, suppose the muscle in the walls of left side of the heart deteriorates. As a result, the left atrium and left ventricle become enlarged, and the heart muscle displays less contractility. This decreases cardiac output of blood through the circulatory system which, in turn, may result in an increased heart rate and less resting time between heartbeats. The heart consumes more energy and oxygen, and its condition typically worsens over a period of time.

In the above example, as the left side of the heart becomes enlarged, the intrinsic electrical heart signals that control heart rhythm are also affected. Normally, such intrinsic signals originate in the sinoatrial (SA) node in the upper right atrium, traveling through and depolarizing the atrial heart tissue such that resulting contractions of the right and left atria are triggered. The intrinsic atrial heart signals are received by the atrioventricular (AV) node which, in turn, triggers a subsequent ventricular intrinsic heart signal that travels through and depolarizes the ventricular heart tissue such that resulting contractions of the right and left ventricles are triggered substantially simultaneously.

In the above example, where the left side of the heart has become enlarged due to congestive heart failure, however, the ventricular intrinsic heart signals may travel through and depolarize the left side of the heart more slowly than in the right side of the heart. As a result, the left and right ventricles do not contract simultaneously, but rather, the left ventricle contracts after the right ventricle. This reduces the pumping efficiency of the heart. Moreover, in the case of left bundle branch block (LBBB), for example, different regions within the left ventricle may not contract together in a coordinated fashion.

Congestive heart failure can be treated by biventricular coordination therapy that provides pacing pulses to both right and left ventricles. See, e.g., Mower U.S. Pat. No. 4,928,688. Congestive heart failure may also result in an overly long atrioventricular (AV) delay between atrial and ventricular contractions, again reducing the pumping efficiency of the heart. There is a need to provide congestive heart failure patients with improved pacing and coordination therapies for improving the AV delay, coordinating ventricular contractions, or otherwise increasing heart pumping efficiency.

Another problem faced by cardiac rhythm management systems is the presence of atrial tachyarrhythmias, such as atrial fibrillation, occurring in patients having congestive heart failure. Atrial fibrillation is a common cardiac arrhythmia that reduces the pumping efficiency of the heart, though not to as great a degree as in ventricular fibrillation. However, this reduced pumping efficiency requires the ventricle to work harder, which is particularly undesirable in congestive heart failure or other sick patients that cannot tolerate additional stresses. Even though a congestive heart failure may have adequate ventricular coordination and cardiac output in the presence of a normal sinus rhythm, when atrial tachyarrhythmia is present, ventricular incoordination may occur, seriously worsening cardiac function.

Moreover, some devices treating congestive heart failure sense atrial heart rate and provide biventricular coordination therapy at a ventricular heart rate that tracks the atrial heart rate. See, e.g., Mower U.S. Pat. No. 4,928,688. Such atrial-tracking devices require a normal sinus rhythm to ensure proper delivery of biventricular coordination therapy. In the presence of atrial tachyarrhythmias, such as atrial fibrillation, however, such atrial tracking biventricular coordination therapy could lead to too-fast and irregular biventricular coordination that is ineffective and even dangerous.

Another problem is that atrial fibrillation may induce irregular ventricular heart rhythms by processes that are yet to be fully understood. Such induced ventricular arrhythmias compromise pumping efficiency even more drastically than atrial arrhythmias. Some devices treating congestive heart failure provide biventricular coordination therapy that does not track the atrial heart rate, but instead, a sensed ventricular contraction in a first ventricle triggers a ventricular pace in the other ventricle, or in both ventricles. See, e.g. Mower U.S. Pat. No. 4,928,688. Even if such biventricular coordination therapy is ventricular-triggered rather than atrial-tracking, the presence of atrial tachyarrhythmias could lead to ventricular arrhythmias, such that the biventricular coordination therapy becomes ineffective and even dangerous because it is too-fast or irregular because of the irregular ventricular heart rate. For these and other reasons, there is a need to provide congestive heart failure patients with improved pacing and coordination therapies for improving the AV delay, coordinating ventricular contractions, or otherwise increasing heart pumping efficiency, even during atrial arrhythmias such as atrial fibrillation.

SUMMARY OF THE INVENTION

The present system provides, among other things, a cardiac rhythm management system including techniques for computing an indicated pacing interval, AV delay, or other timing interval. In one embodiment, a variable indicated pacing interval is computed based at least in part on an underlying intrinsic heart rate. The indicated pacing interval is used to time the delivery of biventricular coordination therapy even when ventricular heart rates are irregular, such as in the presence of atrial fibrillation. In another embodiment, a variable filter indicated AV interval is computed based at least in part on an underlying intrinsic AV interval. The indicated AV interval is used to time the delivery of atrial tracking biventricular coordination therapy when atrial heart rhythms are not arrhythmic. Other indicated timing intervals may be similarly determined. The indicated pacing interval, AV delay, or other timing interval can also be used in combination with a sensor indicated rate indicator.

In one embodiment, the system includes a first method. Actual timing intervals between cardiac events are obtained. The system computes a first indicated timing interval based at least on a most recent actual timing interval duration and a previous value of the first indicated timing interval. The system provides pacing therapy based on the first indicated timing interval.

In another embodiment, the system includes a second method. The system obtains atrio-ventricular (AV) intervals between atrial events and successive ventricular events. The system computes a first indicated AV interval based at least on a most recent AV interval duration and a previous value of the first indicated AV interval. The system provides pacing therapy based on the first indicated AV interval.

In another embodiment, the system includes a third method. The system obtains V-V intervals between ventricular beats. The system computes a first indicated pacing interval based at least on a most recent V-V interval duration and a previous value of the first indicated pacing interval. The system provides pacing therapy to first and second ventricles, based on the first indicated pacing interval.

Another embodiment provides a cardiac rhythm management system that includes a sensing circuit for sensing events, a controller obtaining timing intervals between events and computing a first indicated timing interval based at least on a most recent actual timing interval duration and a previous value of the first indicated timing interval, and a therapy circuit, providing pacing therapy based on the first indicated timing interval.

Another embodiment provides a cardiac rhythm management system that includes at least one ventricular sensing circuit, a controller, and a ventricular therapy circuit. The controller includes a V-V interval timer obtaining V-V intervals between successive events in at least one ventricle, a first register for storing a first indicated pacing interval, and a filter updating the first indicated pacing interval based on a most recent V-V interval provided by the VV interval timer and previous value of the first indicated pacing interval stored the first register. The ventricular therapy circuit provides pacing therapy to first and second ventricles based at least partially on the first indicated pacing interval. Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

Figure 1:
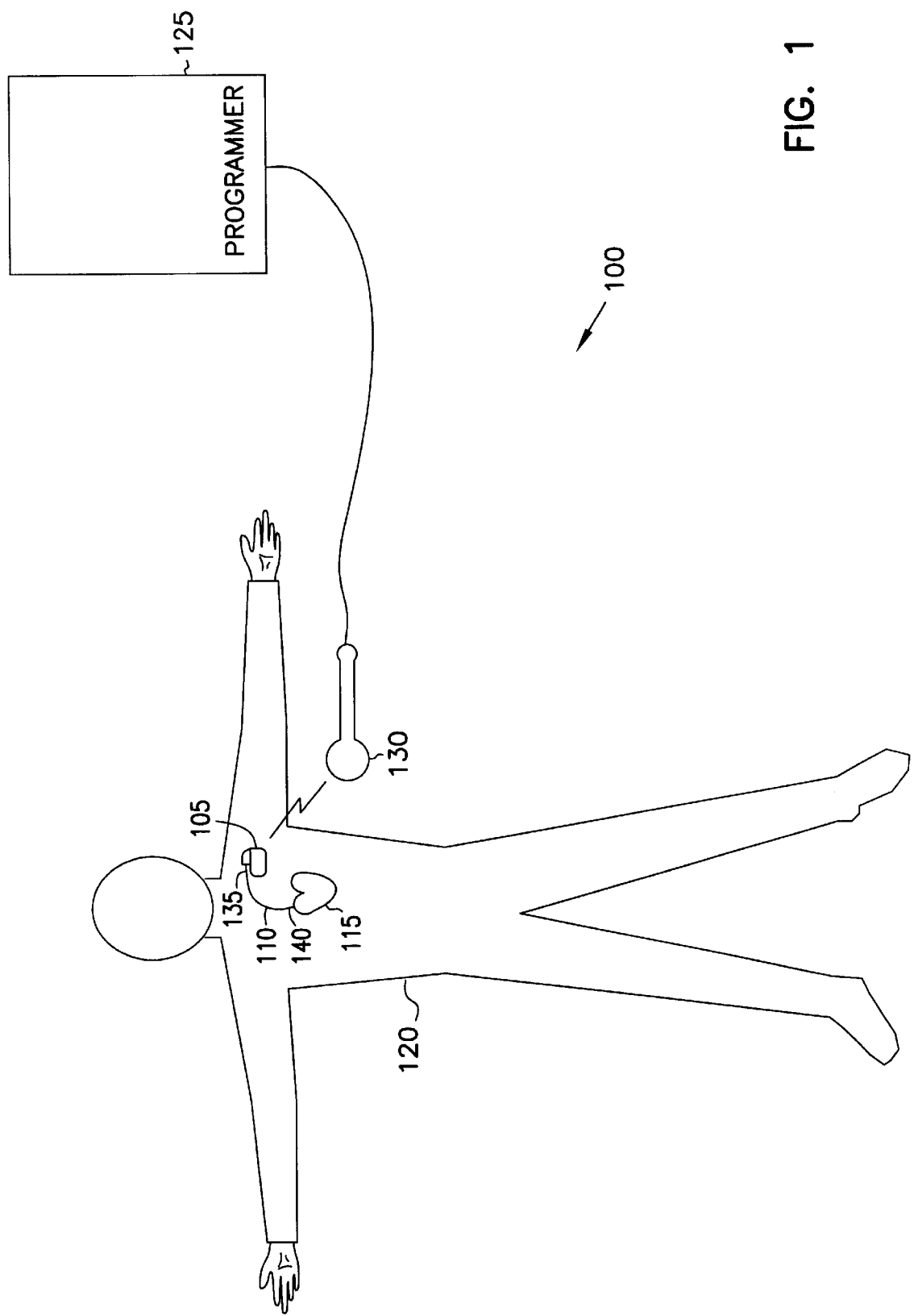
FIG. 1 is a schematic drawing illustrating generally one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components.

The present methods and apparatus will be described in applications involving implantable medical devices including, but not limited to, implantable cardiac rhythm management systems such as pacemakers, cardioverter/defibrillators, pacer/defibrillators, and biventricular or other multi-site coordination devices. However, it is understood that the present methods and apparatus may be employed in unimplanted devices, including, but not limited to, external pacemakers, cardioverter/defibrillators, pacer/defibrillators, biventricular or other multi-site coordination devices, monitors, programmers and recorders.

Problems Associated with Atrial Arrhythmias

As stated earlier, one potential cause of irregularity of ventricular contractions arises during atrial tachyarrhythmias, such as atrial fibrillation. During atrial fibrillation, irregular ventricular contractions may be caused by an atrial tachyarrhythmia that is conducted to the ventricles. Pacing the ventricles regularizes the ventricular heart rate by establishing retrograde conduction from the ventricles. This, in turn, is believed to block forward conduction of atrial signals through the atrioventricular (A-V) node. As a result, irregular atrial signals do not trigger resulting irregular ventricular contractions.

One therapy for treating irregular ventricular contractions during atrial fibrillation is to increase the ventricular heart rate by pacing the ventricles at a higher rate than the average unpaced (intrinsic) ventricular heart rate. Such therapy improves cardiac output because it stabilizes the rate of ventricular contractions to avoid short periods between contractions and/or long periods without a contraction. Such therapy is also believed to decrease the ability of the atrial fibrillation to induce irregular ventricular contractions. Additionally, pacing the ventricles at above the average intrinsic ventricular heart rate can provide coordination therapy. Coordination therapy applies the pacing stimulation to one ventricle at multiple sites, to both ventricles at a single site in each ventricle, or to both ventricles at multiple sites in each ventricle. Coordination therapy is applied to the sites in a fashion that coordinates the sequence of contraction in ventricular heart tissue. Coordination therapy is believed to increase systolic pulse pressure in patients with ventricular conduction disorders, such as left bundle branch block (LBBB), associated with uncoordinated ventricular contractions. Coordination therapy also decreases the time required for systolic contraction, leaving more time for diastolic ventricular filling, thereby also improving the end diastolic pressure.

Ventricular Rate Regularization (VRR) Example

This document describes, among other things, a cardiac rhythm management system providing a method and apparatus for treating irregular ventricular contractions during atrial arrhythmia by actively stabilizing the ventricular heart rate to obtain less potentially proarrhythmic conditions for delivering the atrial tachyarrhythmia therapy. One suitable technique for stabilizing ventricular heart rate is referred to as Ventricular Rate Regularization, described in Krig et al. U.S. patent application Ser. No. 09/316,515 entitled "Method and Apparatus for Treating Irregular Ventricular Contractions Such As During Atrial Arrhythmia," which is filed on even date herewith, assigned to the assignee of the present patent application, and which is herein incorporated by reference in its entirety.

FIG. 1 is a schematic drawing illustrating, by way of example, but not by way of limitation, one embodiment of portions of a cardiac rhythm management system 100 and an environment in which it is used. In FIG. 1, system 100 includes an implantable cardiac rhythm management device 105, also referred to as an electronics unit, which is coupled by an intravascular endocardial lead 110, or other lead, to a heart 115 of patient 120. System 100 also includes an external programmer 125 providing wireless communication with device 105 using a telemetry device 130. Catheter lead 110 includes a proximal end 135, which is coupled to device 105, and a distal end 140, which is coupled to one or more portions of heart 115.

Figure 2:
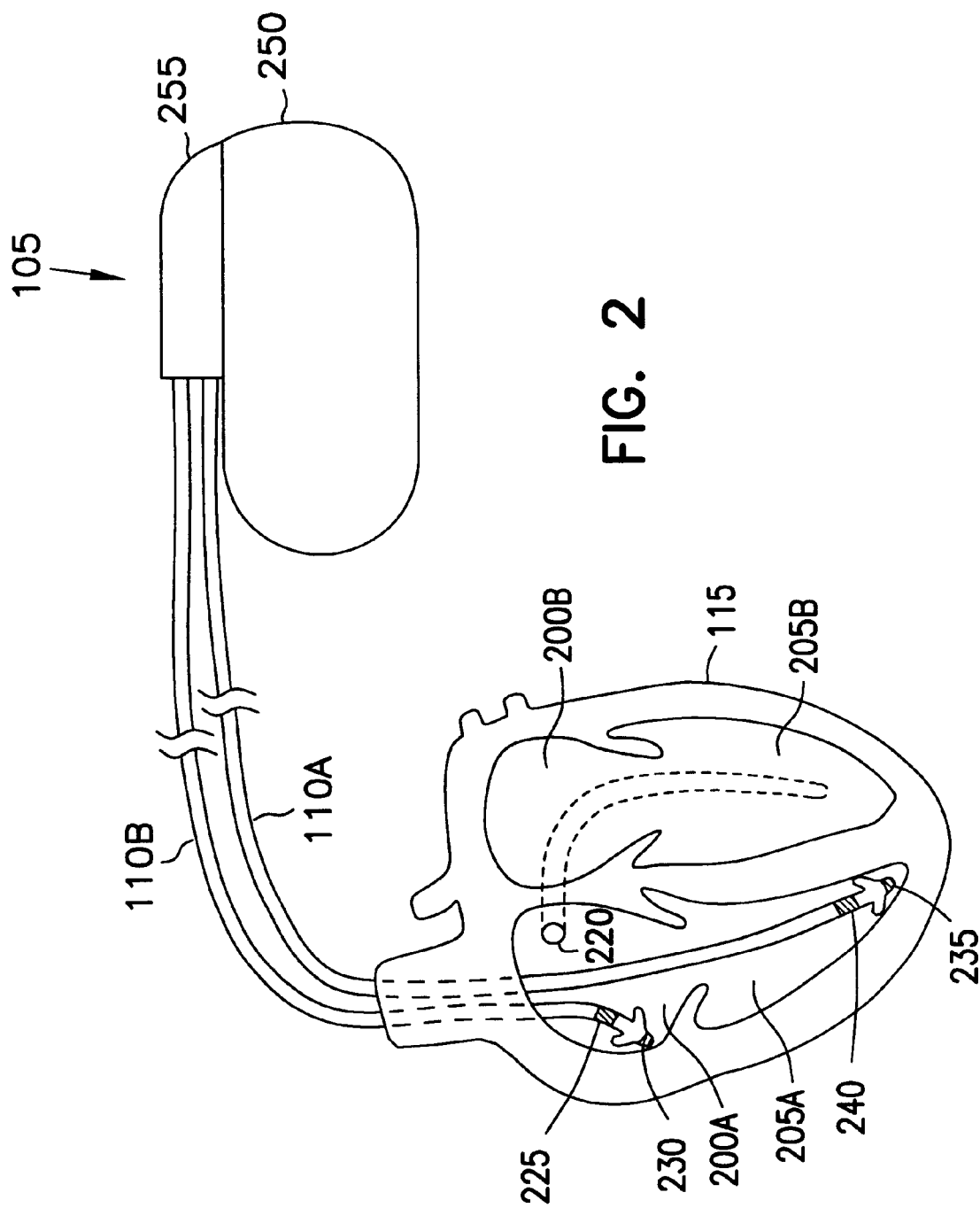
FIG. 2 is a schematic drawing illustrating one embodiment of a cardiac rhythm management device coupled by leads to a heart.

FIG. 2 is a schematic drawing illustrating, by way of example, but not by way of limitation, one embodiment of device 105 coupled by leads 110A–B to heart 115, which includes a right atrium 200A, a left atrium 200B, a right ventricle 205A, a left ventricle 205B, and a coronary sinus 220 extending from right atrium 200A. In this embodiment, atrial lead 110A includes electrodes (electrical contacts) disposed in, around, or near an atrium 200 of heart 115, such as ring electrode 225 and tip electrode 230, for sensing signals and/or delivering pacing therapy to the atrium 200. Lead 110A optionally also includes additional electrodes, such as for delivering atrial and/or ventricular cardioversion/defibrillation and/or pacing therapy to heart 115.

In FIG. 2, a ventricular lead 110B includes one or more electrodes, such as tip electrode 235 and ring electrode 240, for delivering sensing signals and/or delivering pacing therapy. Lead 110B optionally also includes additional electrodes, such as for delivering atrial and/or ventricular cardioversion/defibrillation and/or pacing therapy to heart 115. Device 105 includes components that are enclosed in a hermetically-sealed can 250. Additional electrodes may be located on the can 250, or on an insulating header 255, or on other portions of device 105, for providing unipolar pacing and/or defibrillation energy in conjunction with the electrodes disposed on or around heart 115. Other forms of electrodes include meshes and patches which may be applied to portions of heart 115 or which may be implanted in other areas of the body to help "steer" electrical currents produced by device 105. The present method and apparatus will work in a variety of configurations and with a variety of electrical contacts or "electrodes."

Example Cardiac Rhythm Management Device

Figure 3:
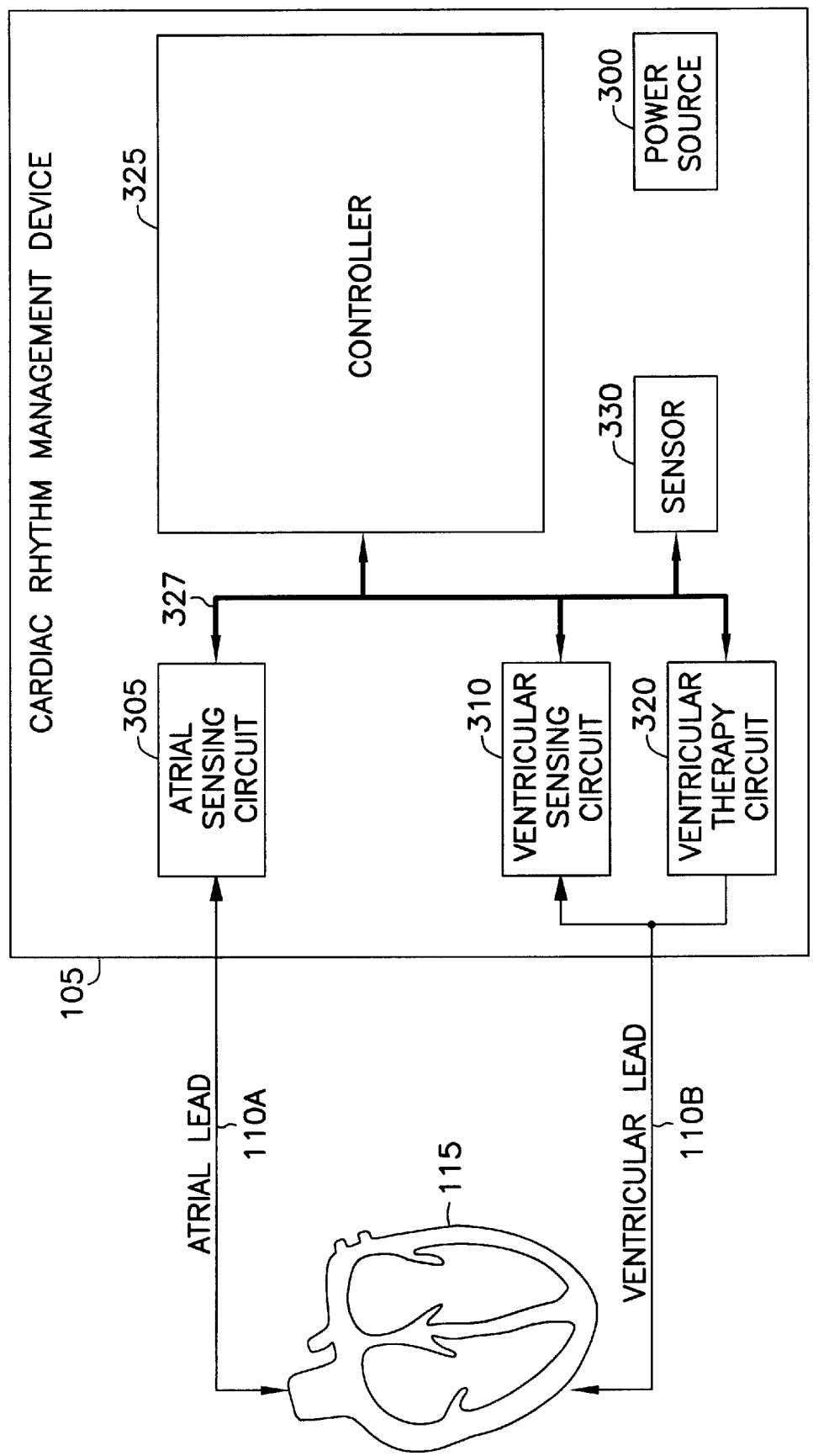
FIG. 3 is a schematic diagram illustrating generally one embodiment of portions of a cardiac rhythm management device coupled to a heart.

FIG. 3 is a schematic diagram illustrating generally, by way of example, but not by way of limitation, one embodiment of portions of device 105, which is coupled to heart 115. Device 105 includes a power source 300, an atrial sensing circuit 305, a ventricular sensing circuit 310, a ventricular therapy circuit 320, and a controller 325.

Atrial sensing circuit 305 is coupled by atrial lead 110A to heart 115 for receiving, sensing, and/or detecting electrical atrial heart signals. Such atrial heart signals include atrial activations (also referred to as atrial depolarizations or P-waves), which correspond to atrial contractions. Such atrial heart signals include normal atrial rhythms, and abnormal atrial rhythms including atrial tachyarrhythmias, such as atrial fibrillation, and other atrial activity. Atrial sensing circuit 305 provides one or more signals to controller 325, via node/bus 327, based on the received atrial heart signals. Such signals provided to controller 325 indicate, among other things, the presence of atrial fibrillation.

Ventricular sensing circuit 310 is coupled by ventricular lead 110B to heart 115 for receiving, sensing, and/or detecting electrical ventricular heart signals, such as ventricular activations (also referred to as ventricular depolarizations or R-waves), which correspond to ventricular contractions. Such ventricular heart signals include normal ventricular rhythms, and abnormal ventricular rhythms, including ventricular tachyarrhythmias, such as ventricular fibrillation, and other ventricular activity, such as irregular ventricular contractions resulting from conducted signals from atrial fibrillation. Ventricular sensing circuit 310 provides one or more signals to controller 325, via node/bus 327, based on the received ventricular heart signals. Such signals provided to controller 325 indicate, among other things, the presence of ventricular depolarizations, whether regular or irregular in rhythm.

Ventricular therapy circuit 320 provides ventricular pacing therapy, as appropriate, to electrodes located at or near one of the ventricles 205 of heart 115 for obtaining resulting evoked ventricular depolarizations. In one embodiment, ventricular therapy circuit 320 also provides cardioversion/defibrillation therapy, as appropriate, to electrodes located at or near one of the ventricles 205 of heart 115, for terminating ventricular fibrillation and/or other ventricular tachyarrhythmias.

Controller 325 controls the delivery of therapy by ventricular therapy circuit 320 and/or other circuits, based on heart activity signals received from atrial sensing circuit 305 and ventricular sensing circuit 310, as discussed below. Controller 325 includes various modules, which are implemented either in hardware or as one or more sequences of steps carried out on a microprocessor or other controller. Such modules are illustrated separately for conceptual clarity; it is understood that the various modules of controller 325 need not be separately embodied, but may be combined and/or otherwise implemented, such as in software/firmware.

In general terms, sensing circuits 305 and 310 sense electrical signals from heart tissue in contact with the catheter leads 110A–B to which these sensing circuits 305 and 310 are coupled. Sensing circuits 305 and 310 and/or controller 325 process these sensed signals. Based on these sensed signals, controller 325 issues control signals to therapy circuits, such as ventricular therapy circuit 320, if necessary, for the delivery of electrical energy (e.g., pacing and/or defibrillation pulses) to the appropriate electrodes of leads 110A–B. Controller 325 may include a microprocessor or other controller for execution of software and/or firmware instructions. The software of controller 325 may be modified (e.g., by remote external programmer 105) to provide different parameters, modes, and/or functions for the implantable device 105 or to adapt or improve performance of device 105.

In one further embodiment, one or more sensors, such as sensor 330, may serve as inputs to controller 325 for adjusting the rate at which pacing or other therapy is delivered to heart 115. One such sensor 330 includes an accelerometer that provides an input to controller 325 indicating increases and decreases in physical activity, for which controller 325 increases and decreases pacing rate, respectively. Another such sensor includes an impedance measurement, obtained from body electrodes, which provides an indication of increases and decreases in the patient's respiration, for example, for which controller 325 increases and decreases pacing rate, respectively. Any other sensor 330 providing an indicated pacing rate can be used.

Figure 4:
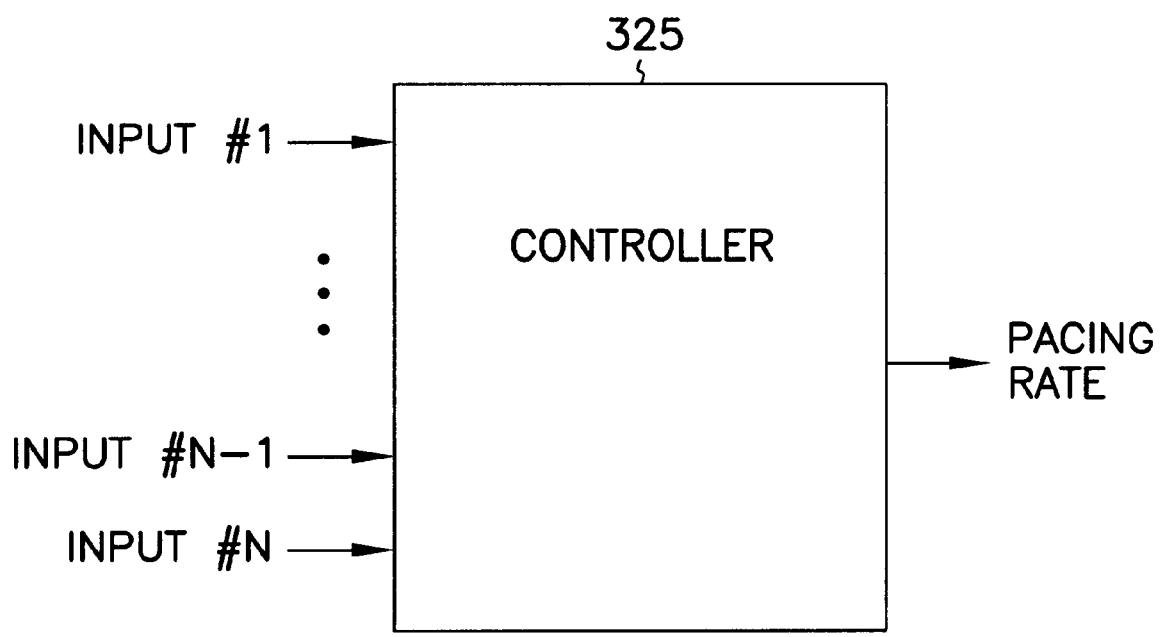
FIG. 4 is a schematic diagram illustrating generally one embodiment of a controller.

FIG. 4 is a schematic diagram illustrating generally, by way of example, but not by way of limitation, one embodiment of controller 325 that includes several different inputs to modify the rate at which pacing or other therapy is delivered. For example, Input #1 may provide information about left ventricular rate, Input #2 may provide an accelerometer-based indication of activity, and Input #3 may provide an impedance-based indication of respiration, such as minute ventilation. Based on at least one of these and/or other inputs, controller 325 provides an output indication of pacing rate as a control signal delivered to a therapy circuit, such as to ventricular therapy circuit 320. Ventricular therapy circuit 320 issues pacing pulses based on one or more such control signals received from controller 325. Control of the pacing rate may be performed by controller 325, either alone or in combination with peripheral circuits or modules, using software, hardware, firmware, or any combination of the like. The software embodiments provide flexibility in how inputs are processed and may also provide the opportunity to remotely upgrade the device software while still implanted in the patient without having to perform surgery to remove and/or replace the device 105.

Controller Example 1

Figure 5:
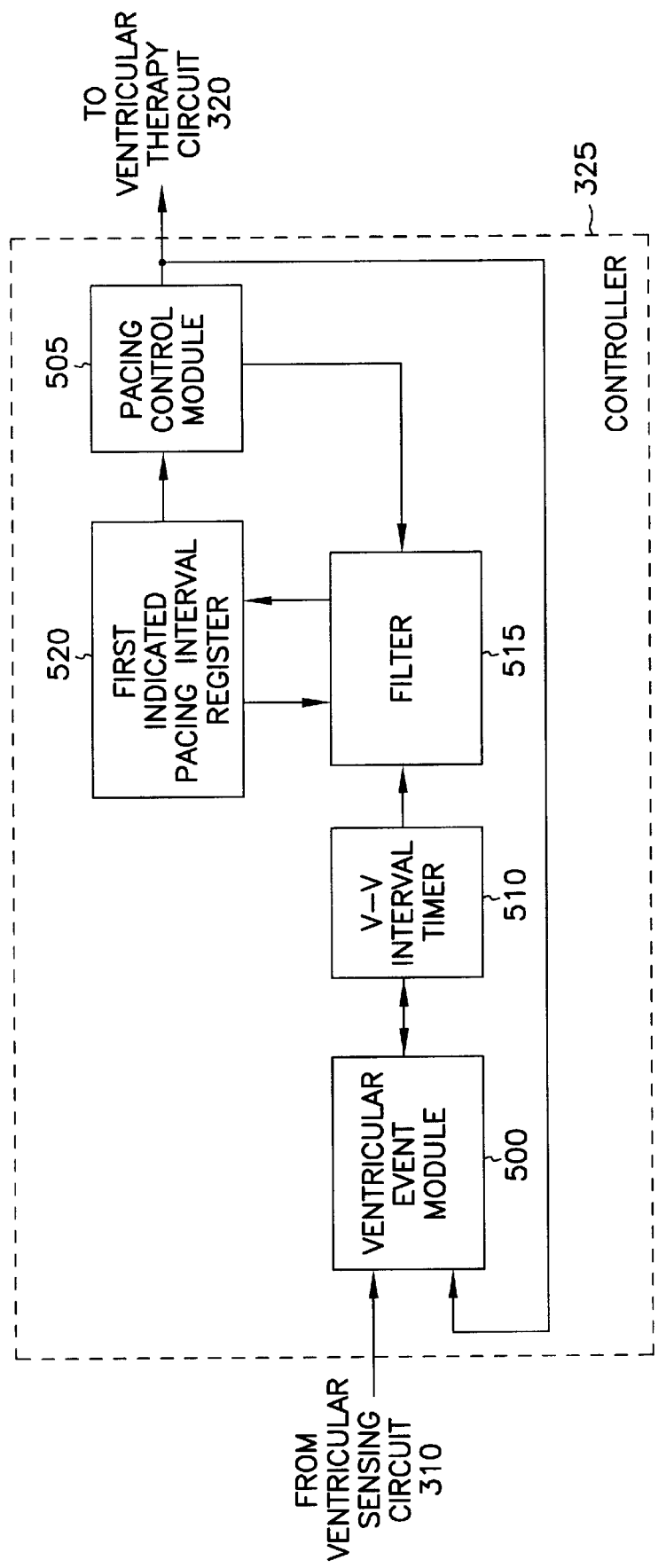
FIG. 5 is a schematic diagram illustrating generally one conceptualization of portions of a controller.

FIG. 5 is a schematic diagram illustrating generally, by way of example, but not by way of limitation, one conceptualization of portions of controller 325. At least one signal from ventricular sensing circuit 310 is received by ventricular event module 500, which recognizes the occurrence of ventricular events included within the signal. Such events are also referred to as "beats," "activations," "depolarizations," "QRS complexes," "R-waves," "contractions." Ventricular event module 500 detects intrinsic events (also referred to as sensed events) from the signal obtained from ventricular sensing circuit 310. Ventricular event module 500 also detects evoked events (resulting from a pace) either from the signal obtained from ventricular sensing circuit 310, or preferably from a ventricular pacing control signal obtained from pacing control module 505, which also triggers the delivery of a pacing stimulus by ventricular therapy circuit 320. Thus, ventricular events include both intrinsic/sensed events and evoked/paced events.

A time interval between successive ventricular events, referred to as a V-V interval, is recorded by a first timer, such as V-V interval timer 510. A filter 515 computes a "first indicated pacing interval," i.e., one indication of a desired time interval between ventricular events or, stated differently, a desired ventricular heart rate. The first indicated pacing interval is also referred to as a ventricular rate regularization (VRR) indicated pacing interval. In various embodiments, filter 515 includes an averager, a weighted averager, a median filter, an infinite (IIR) filter, a finite impulse response (FIR) filter, or any other analog or digital signal processing circuit providing the desired signal processing described more particularly below.

In one embodiment, filter 515 computes a new value of the first indicated pacing interval based on the duration of the most recent V-V interval recorded by timer 510 and on a previous value of the first indicated pacing interval stored in first indicated pacing interval register 520. Register 520 is then updated by storing the newly computed first indicated pacing interval in register 520. Based on the first indicated pacing interval stored in register 520, pacing control module 505 delivers control signals to ventricular therapy circuit 320 for delivering therapy, such as pacing stimuli, at the VRR-indicated ventricular heart rate corresponding to the inverse of the duration of the first indicated pacing interval.

Filter Example 1

In general terms, for one embodiment, device 105 obtains V-V intervals between successive sensed or evoked ventricular beats. Device 105 computes a new first indicated pacing interval based at least in part on the duration of the most recent V-V interval and a previous value of the first indicated pacing interval. Device 105 provides pacing therapy delivered at a rate corresponding to the inverse of the duration of the first indicated pacing interval.

Figure 6:
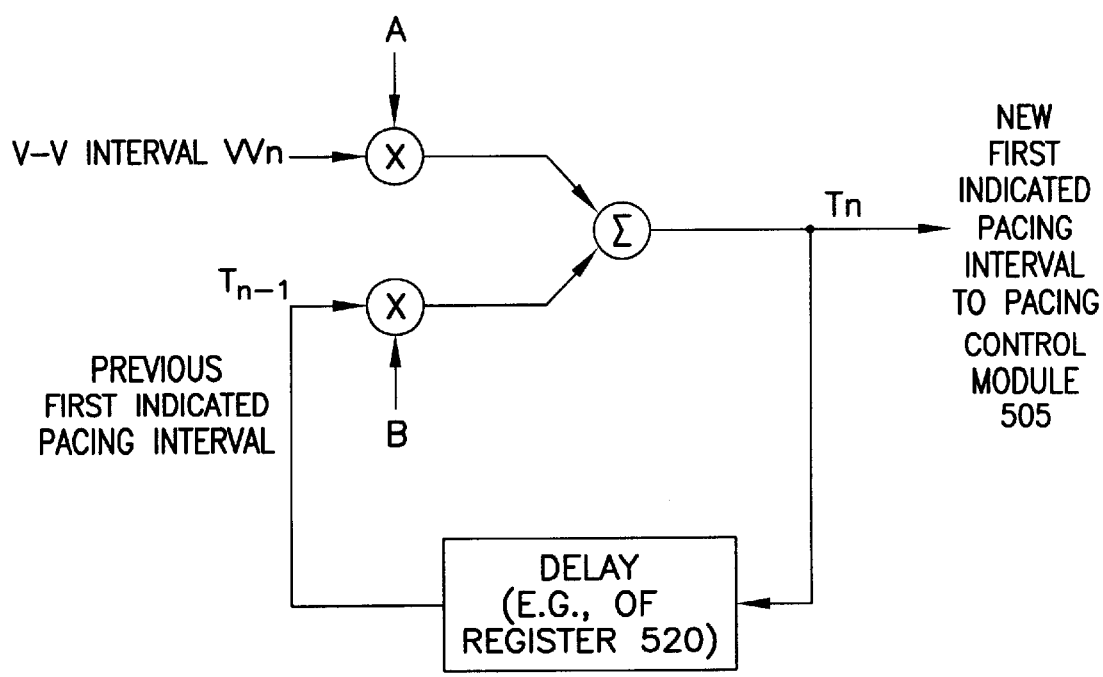
FIG. 6 is a signal flow diagram illustrating generally one conceptual embodiment of operating a filter.

FIG. 6 is a signal flow diagram illustrating generally, by way of example, but not by way of limitation, one embodiment of operating filter 515. Upon the occurrence of a sensed or evoked ventricular beat, timer 510 provides filter 515 with the duration of the V-V interval concluded by that beat, which is referred to as the most recent V-V interval ($VV_n$). Filter 515 also receives the previous value of the first indicated pacing interval ($T_{n-1}$) stored in register 520. The most recent V-V interval $VV_n$ and the previous value of the first indicated pacing interval $T_{n-1}$ are each scaled by respective constants A and B, and then summed to obtain a new value of the first indicated pacing interval ($T_n$), which is stored in register 520 and provided to pacing control module 505. In one embodiment, the coefficients A and B are different values, and are either programmable, variable, or constant.

If no ventricular beat is sensed during the new first indicated pacing interval $T_n$, which is measured as the time from the occurrence of the ventricular beat concluding the most recent V-V interval $VV_n$, then pacing control module 505 instructs ventricular therapy circuit 320 to deliver a ventricular pacing pulse upon the expiration of the new first indicated pacing interval $T_n$. In one embodiment, operation of the filter is described by $T_n = A \cdot VV_n + B \cdot T_{n-1}$, where A and B are coefficients (also referred to as "weights"), $VV_n$ is the most recent V-V interval duration, and $T_{n-1}$ is the previous value of the first indicated pacing interval.

Initialization of filter 515 includes seeding the filter by storing, in register 520, an initial interval value. In one embodiment, register 520 is initialized to an interval value corresponding to a lower rate limit (LRL), i.e., a minimum rate at which pacing pulses are delivered by device 105. Register 520 could alternatively be initialized with any other suitable value.

Filter Example 2

In one embodiment, operation of filter 515 is based on whether the beat concluding the most recent V-V interval $VV_n$ is a sensed/intrinsic beat or a paced/evoked beat. In this embodiment, the pacing control module 505, which controls the timing and delivery of pacing pulses, provides an input to filter 515 that indicates whether the most recent V-V interval $VV_n$ was concluded by an evoked beat initiated by a pacing stimulus delivered by device 105, or was concluded by an intrinsic beat sensed by ventricular sensing circuit 310.

In general terms, if the most recent V-V interval $VV_n$ is concluded by a sensed/intrinsic beat, then filter 515 provides a new first indicated pacing interval $T_n$ that is adjusted from the value of the previous first indicated pacing interval $T_{n-1}$ such as, for example, decreased by an amount that is based at least partially on the duration of the most recent V-V interval $VV_n$ and on the duration of the previous value of the first indicated pacing interval $T_{n-1}$. If, however, the most recent V-V interval $VV_n$ is concluded by a paced/evoked beat, then filter 515 provides a new first indicated pacing interval $T_n$ that is increased from the value of the previous first indicated pacing interval $T_{n-1}$, such as, for example, by an amount that is based at least partially on the duration of the most recent V-V interval $VV_n$ and on the duration of the previous value of the first indicated pacing interval $T_{n-1}$. If no ventricular beat is sensed during the new first indicated pacing interval $T_n$, which is measured as the time from the occurrence of the ventricular beat concluding the most recent V-V interval $VV_n$, then pacing control module 505 instructs ventricular therapy circuit 320 to deliver a ventricular pacing pulse upon the expiration of the new first indicated pacing interval $T_n$.

Figure 7:
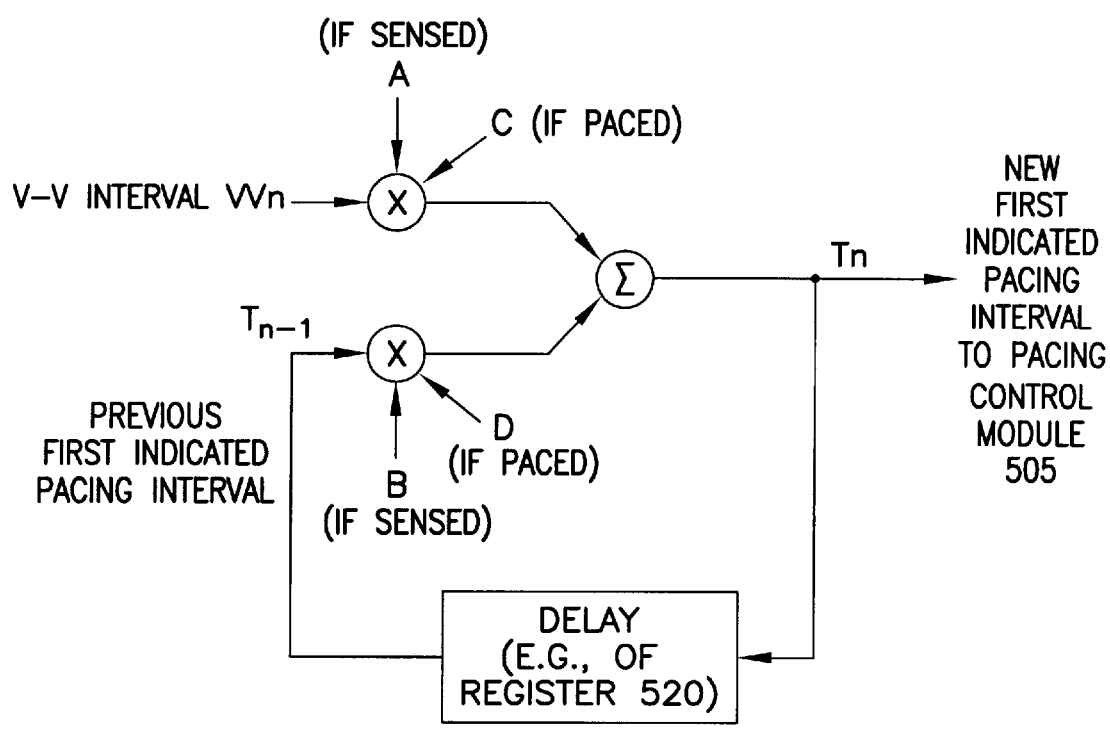
FIG. 7 is a signal flow diagram illustrating generally another conceptualization of operating the filter.

FIG. 7 is a signal flow diagram, illustrating generally, by way of example, but not by way of limitation, another conceptualization of operating filter 515, with certain differences from FIG. 6 more particularly described below. In this embodiment, the pacing control module 505, which controls the timing and delivery of pacing pulses, provides an input to filter 515 that indicates whether the most recent V-V interval $VV_n$ was concluded by an evoked beat initiated by a pacing stimulus delivered by device 105, or was concluded by an intrinsic beat sensed by ventricular sensing circuit 310.

If the most recent V-V interval $VV_n$ was concluded by an intrinsic beat, then the most recent V-V interval $VV_n$ and the previous value of the first indicated pacing interval $T_{n-1}$ are each scaled by respective constants A and B, and then summed to obtain the new value of the first indicated pacing interval $T_n$, which is stored in register 520 and provided to pacing control module 505. Alternatively, if the most recent V-V interval $VV_n$ was concluded by a evoked/paced beat, then the most recent V-V interval $VV_n$ and the previous value of the first indicated pacing interval $T_{n-1}$ are each scaled by respective constants C and D, and then summed to obtain the new value of the first indicated pacing interval $T_n$, which is stored in register 520 and provided to pacing control module 505. In one embodiment, the coefficients C and D are different from each other, and are either programmable, variable, or constant. In a further embodiment, the coefficient C is a different value from the coefficient A, and/or the coefficient D is a different value than the coefficient B, and these coefficients are either programmable, variable, or constant. In another embodiment, the coefficient D is the same value as the coefficient B.

In one embodiment, operation of filter 515 is described by $T_n = A \cdot VV_n + B \cdot T_{n-1}$, if $VV_n$ is concluded by an intrinsic beat, and is described by $T_n = C \cdot VV_n + D \cdot T_{n-1}$, if $VV_n$ is concluded by a paced beat, where A, B, C and D are coefficients (also referred to as "weights"), $VV_n$ is the most recent V-V interval duration, $T_n$ is the new value of the first indicated pacing interval, and $T_{n-1}$ is the previous value of the first indicated pacing interval. If no ventricular beat is sensed during the new first indicated pacing interval $T_n$, which is measured as the time from the occurrence of the ventricular beat concluding the most recent V-V interval $VV_n$, then pacing control module 505 instructs ventricular therapy circuit 320 to deliver a ventricular pacing pulse upon the expiration of the new first indicated pacing interval $T_n$.

Filter Example 3

Figure 8:
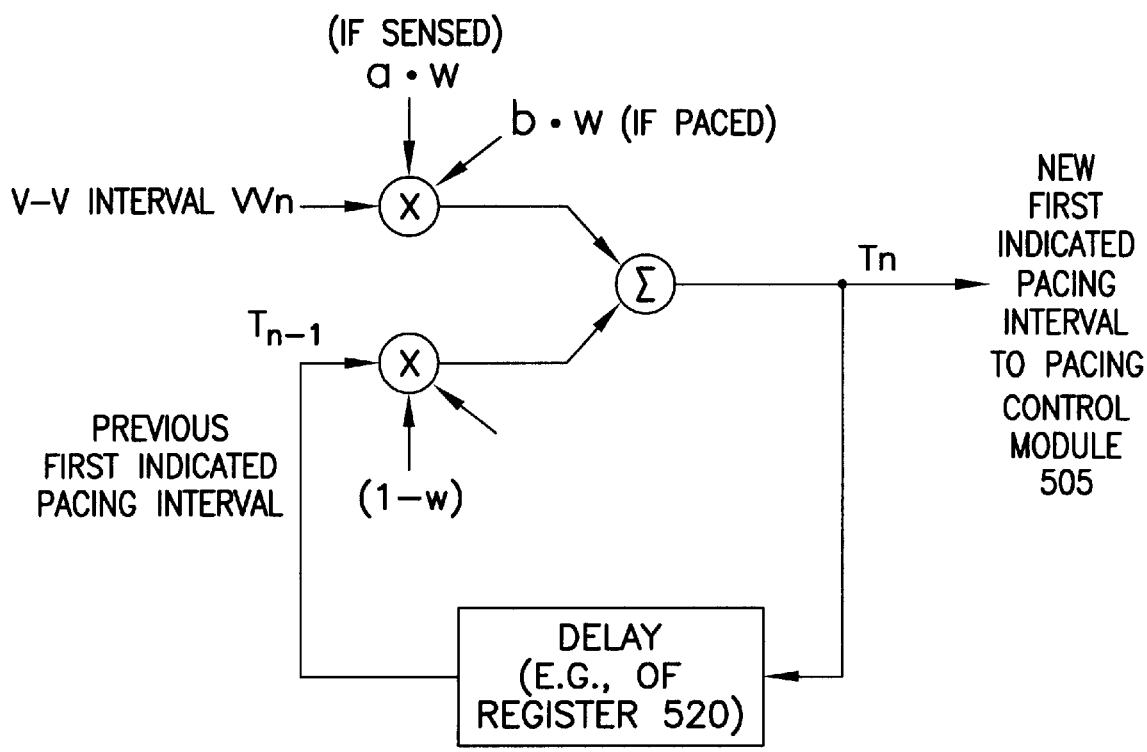
FIG. 8 is a signal flow diagram illustrating generally a further conceptualization of operating the filter.

In another embodiment, these coefficients can be more particularly described using an intrinsic coefficient (a), a paced coefficient (b), and a weighting coefficient (w). In one such embodiment, $A = a \cdot w$, $B = (1-w)$, $C = b \cdot w$, and $D = (1-w)$. In one example, operation of the filter 515 is described by $T_n = a \cdot w \cdot VV_n + (1-w) \cdot T_{n-1}$, if $VV_n$ is concluded by an intrinsic beat, otherwise is described by $T_n = b \cdot w \cdot VV_n + (1-w) \cdot T_{n-1}$, if $VV_n$ is concluded by a paced beat, as illustrated generally, by way of example, but not by way of limitation, in the signal flow graph of FIG. 8. If no ventricular beat is sensed during the new first indicated pacing interval $T_n$, which is measured as the time from the occurrence of the ventricular beat concluding the most recent V-V interval $VV_n$, then pacing control module 505 instructs ventricular therapy circuit 320 to deliver a ventricular pacing pulse upon the expiration of the new first indicated pacing interval $T_n$. In one embodiment, the coefficients a and b are different from each other, and are either programmable, variable, or constant.

The above-described parameters (e.g., A, B, C, D, a, b, w) are stated in terms of time intervals (e.g., $VV_n$, $T_n$, $T_{n-1}$). However, an alternate system may produce results in terms of rate, rather than time intervals, without departing from the present method and apparatus. In one embodiment, weighting coefficient w, intrinsic coefficient a, and paced coefficient b, are variables. Different selections of w, a, and b, will result in different operation of the present method and apparatus. For example, as w increases the weighting effect of the most recent V-V interval $VV_n$ increases and the weighting effect of the previous first indicated pacing rate $T_{n-1}$ decreases. In one embodiment, $w = 1/16 = 0.0625$. In another embodiment, $w = 1/32$. Another possible range for w is from $w = 1/2$ to $w = 1/1024$. A further possible range for w is from $w \approx 0$ to $w \approx 1$. Other values of w, which need not include division by powers of two, may be substituted without departing from the present method and apparatus.

In one embodiment, intrinsic coefficient a, is selected to be greater than 0.5, or to be greater than 1.0. In one example, the intrinsic coefficient a is selected to be lesser in value than the pacing coefficient b. In one example, $a \approx 1.1$ and $b \approx 1.2$. In another embodiment $a = 0.9$ and $b = 1.1$. One possible range for a is from $a = 0.5$ to $a = 2.0$, and for b is from $b = 1.0$ to $b = 3.0$. The coefficients may vary without departing from the present method and apparatus.

In one embodiment, for $b > 1$ and for substantially regular V-V intervals, filter 515 provides a new first indicated pacing interval $T_n$ that is at least slightly longer than the expected intrinsic V-V interval being measured by timer 515. Thus, if the intrinsic V-V interval being timed is consistent with the duration of previously received V-V intervals, then filter 515 avoids triggering a pacing stimulus. In such a case, a pacing pulse is delivered only if the presently timed V-V interval becomes longer than the previous substantially constant V-V intervals. In general terms, filter 515 operates so that pacing pulses are typically inhibited if the ventricular rate is substantially constant. However, if the measured V-V intervals become irregular, then filter 515 operates, over a period of one or several such V-V intervals, to shorten the first indicated pacing interval $T_n$ so that pacing stimuli are being delivered.

According to one aspect of the invention, it is believed that if the irregular V-V intervals are caused by a conducted atrial tachyarrhythmia, then pacing the ventricle will regularize the ventricular heart rate by establishing retrograde conduction from the ventricle. This, in turn, blocks forward conduction of atrial signals through the atrioventricular (A-V) node. As a result, irregular atrial signals do not trigger resulting irregular ventricular contractions. According to another aspect of the invention, however, this method and apparatus will not introduce pacing pulses until the heartbeat becomes irregular. Therefore, the heart is assured to pace at its intrinsic rate when regular ventricular contractions are sensed.

Controller Example 2

Figure 9:
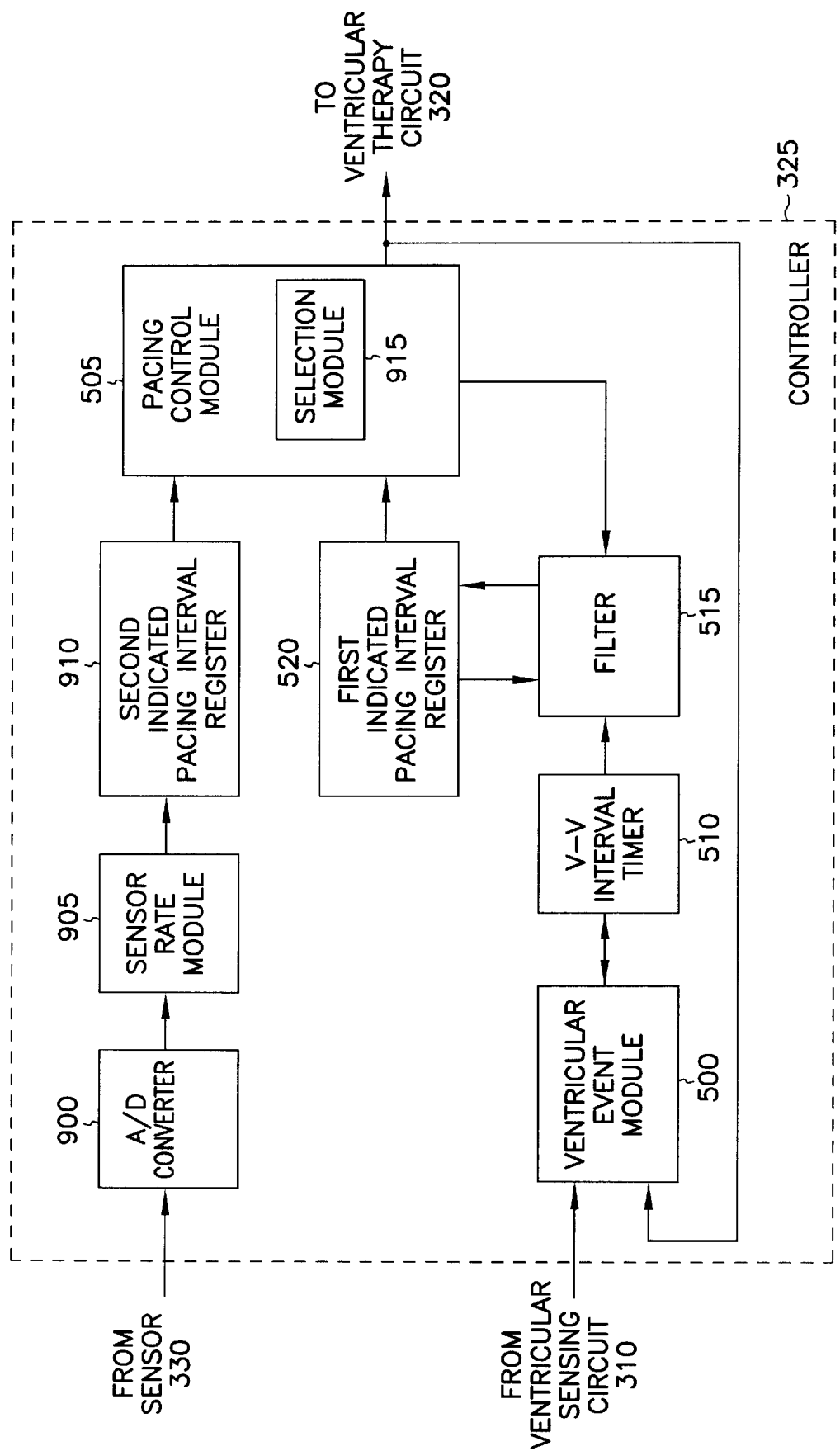
FIG. 9 is a schematic diagram illustrating generally another conceptualization of portions of a controller.

FIG. 9 is a schematic diagram illustrating generally, by way of example, but not by way of limitation, another conceptualization of portions of controller 325, with certain differences from FIG. 5 more particularly described below. In FIG. 9, controller 325 receives from sensor 330 a signal including information from which a physiologically desired heart rate (e.g., based on the patient's activity, respiration, or any other suitable indicator of metabolic need) can be derived. The sensor signal is digitized by an A/D converter 900. The digitized signal is processed by a sensor rate module 905, which computes a desired heart rate that is expressed in terms of a second indicated pacing interval stored in register 910.

Pacing control module 505 delivers a control signal, which directs ventricular therapy circuit 320 to deliver a pacing pulse, based on either (or both) of the first or second indicated pacing intervals, stored in registers 520 and 910, respectively, or both. In one embodiment, pacing control module 505 includes a selection module 915 that selects between the new first indicated pacing interval $T_n$ and the sensor-based second indicated pacing interval.

In one embodiment, selection module 915 selects the shorter of the first and second indicated pacing intervals as the selected indicated pacing interval $S_n$. If no ventricular beat is sensed during the selected indicated pacing interval $S_n$, which is measured as the time from the occurrence of the ventricular beat concluding the most recent V-V interval $VV_n$, then pacing control module 505 instructs ventricular therapy circuit 320 to deliver a ventricular pacing pulse upon the expiration of the selected indicated pacing interval $S_n$.

In general terms, for this embodiment, the ventricle is paced at the higher of the sensor indicated rate and the VRR indicated rate. If, for example, the patient is resting, such that the sensor indicated rate is lower than the patient's intrinsic rate, and the patient's intrinsic rate is substantially constant, then the intrinsic rate is higher than the VRR indicated rate. As a result, pacing pulses generally will not be delivered. But if, for example, the patient is resting, but with an atrial tachyarrhythmia that induces irregular ventricular contractions, then pacing pulses generally will be delivered at the VRR indicated rate. In another example, if the patient is active, such that the sensor indicated rate is higher than the VRR indicated rate, then pacing pulses generally will be delivered at the sensor indicated rate. In an alternative embodiment, the pacing rate is determined by blending the sensor indicated rate and the VRR indicated rate, rather than by selecting the higher of these two indicated rates (i.e., the shorter of the first and second indicated pacing intervals).

In another embodiment, selection module 915 provides a selected indicated pacing interval $S_n$ based on a blending of both the first and second indicated pacing intervals. In one such example, selection module 915 applies predetermined or other weights to the first and second indicated pacing intervals to compute the selected pacing interval $S_n$.

Controller Example 2

Figure 10:
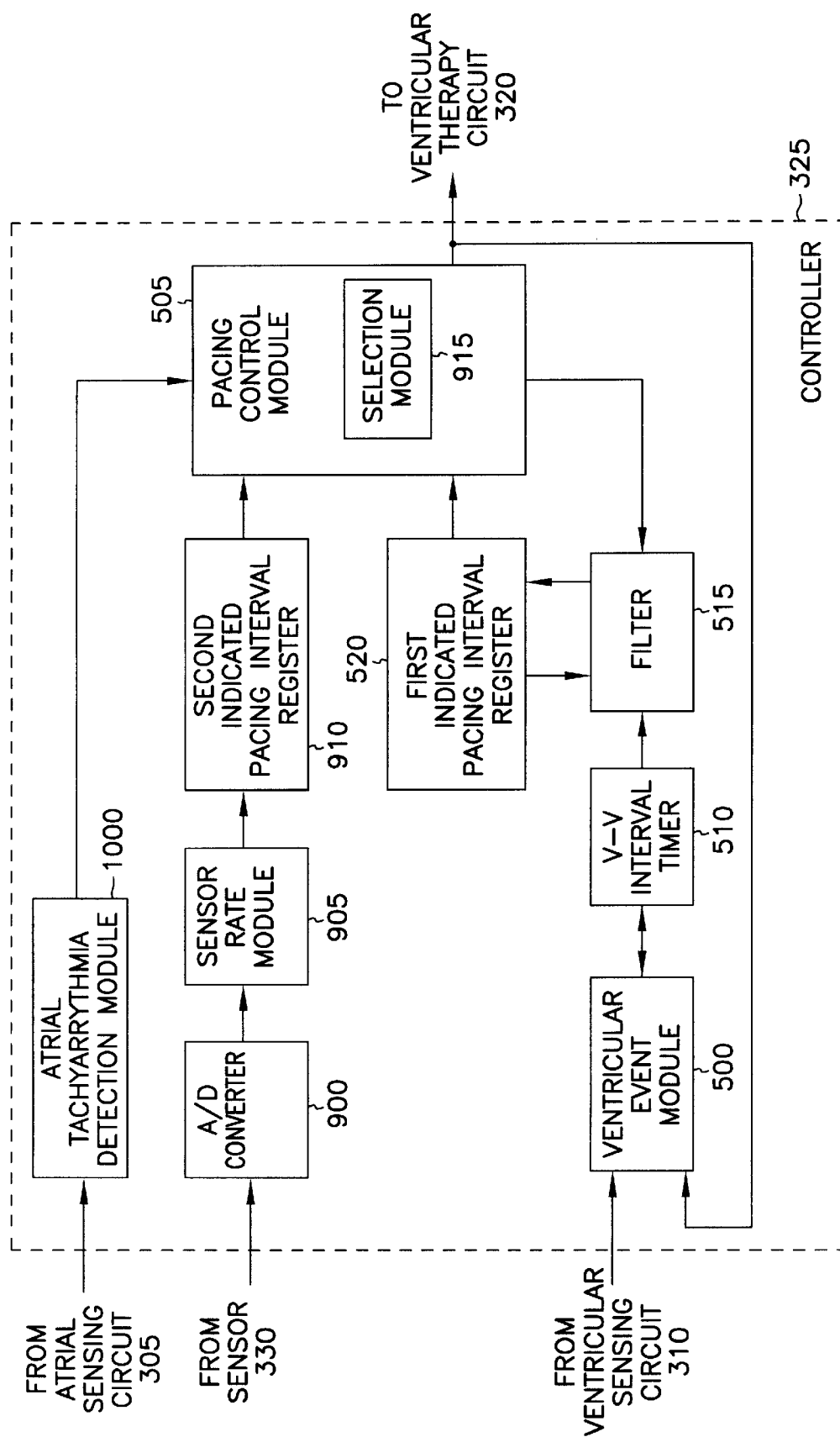
FIG. 10 is a schematic diagram illustrating generally a further conceptualization of portions of a controller.

FIG. 10 is a schematic diagram illustrating generally, by way of example, but not by way of limitation, another conceptualization of portions of controller 325, with certain differences from FIG. 9 more particularly described below. In FIG. 10, controller 325 includes an atrial tachyarrhythmia (AT) detection module 1000 that receives a signal from atrial sensing circuit 305. The received signal includes information about atrial events, from which AT detection module 1000 determines the presence or absence of one or more atrial tachyarrhythmias, such as atrial fibrillation.

In one embodiment, AT detection module 1000 provides a control signal, to pacing control module 505, that indicates the presence or absence of an atrial tachyarrhythmia, such as atrial fibrillation. In one embodiment, selection module 915 selects between the first and second indicated pacing intervals as illustrated, by way of example, but not by way of limitation, in Table 1.

TABLE 1

Example Selection Based on AT Detection, 1st Indicated Pacing Interval, and 2nd Indicated Pacing Interval

| AT Present? | 1st Indicated Pacing Interval < 2nd Indicated Pacing Interval? | 1st Indicated Pacing Interval ≧ 2nd Indicated Pacing Interval? |
|---|---|---|
| Yes, AT Present | $S_n$ ← 1st Indicated Pacing Interval (i.e., VRR) | $S_n$ ← 2nd Indicated Pacing Interval (e.g., Sensor) |
| No, AT not Present | $S_n$ ← 2nd Indicated Pacing Interval (e.g., Sensor) | $S_n$ ← 2nd Indicated Pacing Interval (e.g., Sensor) |

In this embodiment, if an atrial tachyarrhythmia is present and the first indicated pacing interval is shorter than the second indicated pacing interval, then selection module 915 selects the first indicated pacing interval, which is based on the VRR techniques described above, as the selected indicated pacing interval $S_n$. Otherwise, selection module 915 selects the second indicated pacing interval, which in one embodiment is based on the sensor indications, as the selected indicated pacing interval $S_n$. As discussed above, if no ventricular beat is sensed during the selected indicated pacing interval $S_n$, which is measured as the time from the occurrence of the ventricular beat concluding the most recent V-V interval $VV_n$, then pacing control module 505 instructs ventricular therapy circuit 320 to deliver a ventricular pacing pulse upon the expiration of the selected indicated pacing interval $S_n$.

Stated differently, for this embodiment, the ventricle is paced at the VRR indicated rate only if an atrial tachyarrhythmia, such as atrial fibrillation, is present and the VRR indicated rate exceeds the sensor indicated rate. Otherwise the ventricle is paced at the sensor indicated rate. If, for example, the patient is resting, such that the sensor indicated rate is lower than the patient's intrinsic rate, and no atrial tachyarrhythmia is present, then the device will sense the intrinsic rate or will deliver ventricular paces at the lower rate limit. But if, for example, the patient is resting, but with an atrial tachyarrhythmia that induces irregular ventricular contractions, then pacing pulses generally will be delivered at the VRR indicated rate. In another example, if the patient is active, such that the sensor indicated rate is higher than the VRR indicated rate, then pacing pulses generally will be delivered at the sensor indicated rate, whether or not atrial tachyarrhythmia is present. As an alternative to the selection described with respect to Table 1, selection module 915 provides a fixed or variable weighting or blending of both the sensor-indicated rate and VRR indicated rate, such that pacing pulses are delivered based on the blended rate.

The second indicated pacing interval need not be based on sensor indications. In one embodiment, for example, the second indicated pacing interval tracks the sensed atrial heart rate when no atrial tachyarrhythmia is present. In this embodiment, selection module 915 performs a mode-switching function in which the first indicated pacing interval is used whenever atrial tachyarrhythmia is present and the second indicated pacing interval (e.g., atrial-tracking) is used when no atrial tachyarrhythmia is present.

In another embodiment, heart rate/interval is used as a trigger to turn on/off use of the first indicated pacing interval (e.g., the VRR indicated pacing interval). In one example, pacing therapy is based on the first indicated pacing interval if the first indicated pacing interval is longer than a first predetermined value, and pacing therapy is substantially independent of the first indicated pacing interval if the first indicated pacing interval is shorter than the first predetermined value. In this example, the VRR indicated pacing interval is used at low heart rates, but not at fast heart rates.

Filter Rate Behavior Example 1

Figure 11:
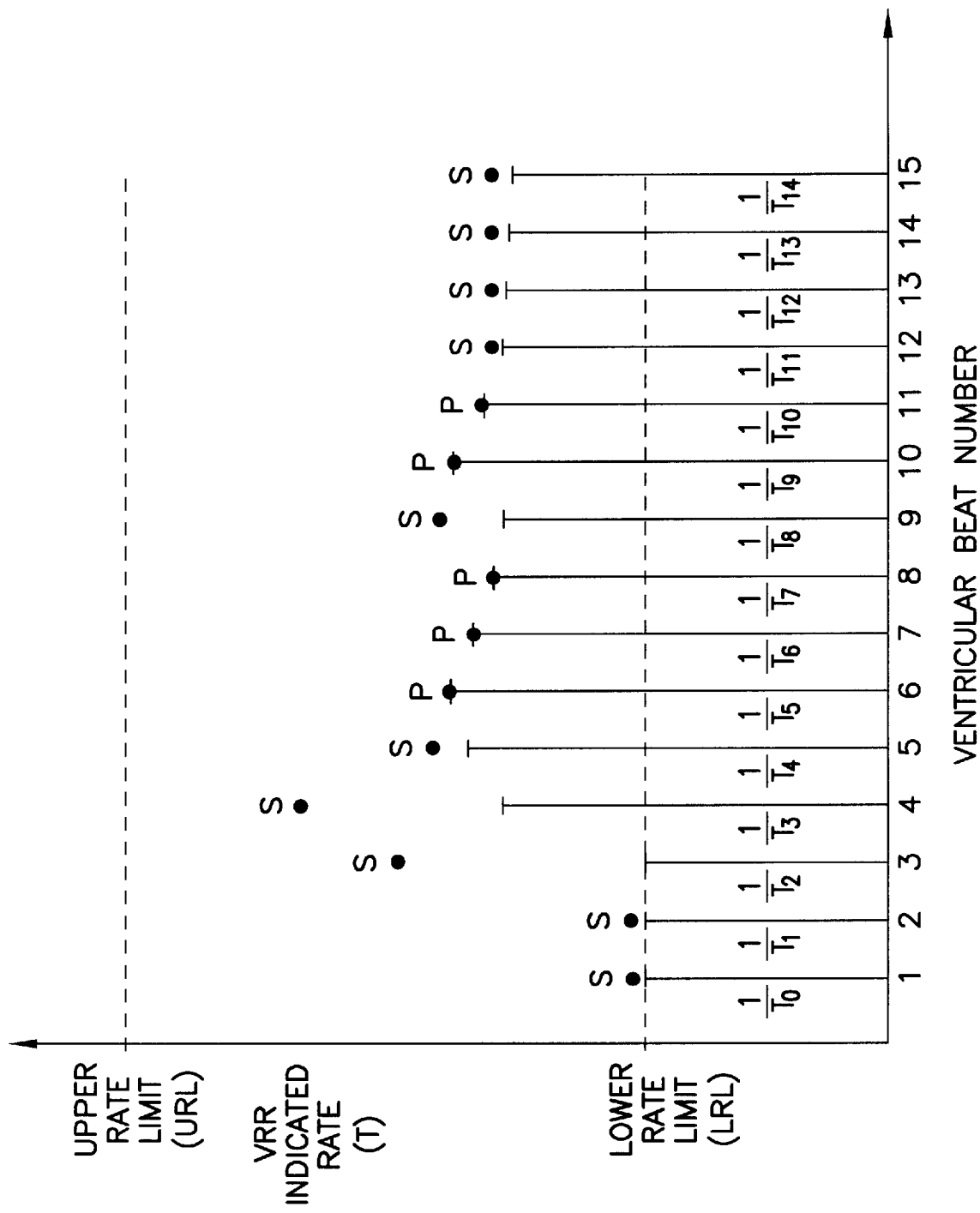
FIG. 11 is a graph illustrating generally one embodiment of operating a filter to provide a first indicated pacing rate, such as a VRR indicated rate, for successive ventricular heart beats.

FIG. 11 is a graph illustrating generally, by way of example, but not by way of limitation, one embodiment of a VRR indicated rate for successive ventricular heart beats for one mode of operating filter 515. As discussed above, the VRR indicated rate is simply the frequency, between ventricular heart beats, associated with the first indicated pacing interval. Stated differently, the VRR indicated rate is the inverse of the duration of the first indicated pacing interval. If pacing is based solely on the VRR indicated rate, pacing control module 505 directs ventricular therapy circuit 320 to issue a pacing pulse after the time since the last ventricular beat equals or exceeds the first indicated pacing interval. However, as described above, in certain embodiments, pacing control module 505 directs ventricular therapy circuit 320 to issue a pacing pulse based on factors other than the VRR indicated rate such as for, example, based on the sensor indicated rate.

In the example illustrated in FIG. 11, a first sensed intrinsic ventricular beat, indicated by an "S" was detected just before expiration of the first indicated pacing interval ("VRR indicated pacing interval") $T_0$, as computed based on a previous ventricular beat. In one embodiment, the new VRR indicated pacing interval $T_1$ is computed based on the duration of most recent V-V interval $VV_1$ and a previous value of the VRR indicated pacing interval $T_0$, as discussed above. In this example, the new VRR indicated pacing interval $T_1$ corresponds to a lower rate limit (LRL) time interval. In one embodiment, the allowable range of the VRR indicated pacing interval is limited so that the VRR indicated pacing interval does not exceed the duration of the LRL time interval, and so that the VRR indicated pacing interval is not shorter than the duration of an upper rate limit (URL) time interval.

The second ventricular beat is also sensed, just before expiration of the VRR indicated pacing interval $T_1$. In one embodiment, the new VRR indicated pacing interval $T_2$ is computed based on the duration of most recent V-V interval $VV_2$ and a previous value of the VRR indicated pacing interval, $T_1$, as discussed above. The first and second ventricular beats represent a stable intrinsic rhythm, for which no pacing is delivered because the VRR indicated pacing interval is at a lower rate than the sensed intrinsic ventricular beats.

The third, fourth, and fifth ventricular beats represent the onset of atrial fibrillation, resulting in erratic ventricular rates. The third ventricular beat is sensed well before expiration of the VRR indicated pacing interval $T_2$, such that no pacing pulse is issued. For the sensed third ventricular beat, filter 515 computes the new VRR indicated pacing interval $T_3$ as being shorter in duration relative to the previous VRR indicated pacing interval $T_2$.

The fourth ventricular beat is similarly sensed well before expiration of the VRR indicated pacing interval $T_3$, such that no pacing pulse is issued. For the sensed fourth ventricular beat, filter 515 computes the new VRR indicated pacing interval $T_4$ as being shorter in duration relative to the previous VRR indicated pacing interval $T_3$.

The fifth ventricular beat is sensed before expiration of the VRR indicated pacing interval $T_4$, such that no pacing pulse is issued. For the sensed fifth ventricular beat, filter 515 computes the new VRR indicated pacing interval $T_5$ as being shorter in duration relative to the previous VRR indicated pacing interval $T_4$.

The sixth, seventh, and eighth ventricular beats indicate regularization of the ventricular rate using the pacing techniques described above. No ventricular beat is sensed during the VRR indicated pacing interval $T_5$, so a pacing pulse is issued to evoke the sixth ventricular beat. A new VRR indicated pacing interval $T_6$ is computed as being increased in duration relative to the previous VRR indicated pacing interval $T_5$, lowering the VRR indicated rate. Similarly, no ventricular beat is sensed during the VRR indicated pacing interval.

The ninth ventricular beat represents another erratic ventricular beat resulting from the atrial fibrillation episode. The ninth ventricular beat is sensed before expiration of the VRR indicated pacing interval $T_8$. As a result, a shorter new VRR indicated pacing interval $T_9$ is computed.

The tenth and eleventh ventricular beats illustrate further regularization of the ventricular rate using the pacing techniques described above. No ventricular beat is sensed during the VRR indicated pacing interval $T_9$, so a pacing pulse is issued to evoke the tenth ventricular beat. A new VRR indicated pacing interval $T_{10}$ is computed as being increased in duration relative to the previous VRR indicated pacing interval $T_9$, lowering the VRR indicated rate. Similarly, no ventricular beat is sensed during the VRR indicated pacing interval $T_{10}$, so a pacing pulse is issued to evoke the tenth ventricular beat. A new VRR indicated pacing interval $T_{11}$ is compute as being increased in duration relative to the previous VRR indicated pacing interval $T_{10}$, lowering the VRR indicated rate.

The twelfth, thirteenth, fourteenth, and fifteenth ventricular beats illustrate resumption of a stable intrinsic rhythm after termination of the atrial fibrillation episode. For such a stable rate, the VRR indicated rate proceeds asymptotically toward a "floor value" that tracks, but remains below, the intrinsic rate. This allows the intrinsic heart signals to control heart rate when such intrinsic heart signals provide a stable rhythm. As a result, when the patient's intrinsic rate is constant, paces will be withheld, allowing the patient's intrinsic heart rhythm to continue. If the patient's heart rate includes some variability, and the VRR indicated floor value is close to the mean intrinsic heart rate, then occasional paced beats will occur. Such pace beats will gradually lengthen the VRR indicated pacing interval, thereby allowing subsequent intrinsic behavior when the patient's heart rate becomes substantially constant.

The intrinsic coefficient a of filter 515 controls the "attack slope" of the VRR indicated heart rate as the VRR indicated heart rate increases because of sensed intrinsic beats. The paced coefficient b of filter 515 controls the "decay slope" of the VRR indicated heart rate as the VRR indicated heart rate decreases during periods of paced beats. In one embodiment, in which a>1.0 and b>1.0, decreasing the value of a toward 1.0 increases the attack slope such that the VRR indicated rate increases faster in response to sensed intrinsic beats, while decreasing the value of b toward 1.0 decreases the decay slope such that the VRR indicated rate decreases more slowly during periods of paced beats. Conversely, for a>1.0 and b>1.0, increasing the value of a from 1.0 decreases the attack slope such that the VRR indicated rate increases more slowly in response to sensed intrinsic beats, while increasing the value of b from 1.0 increases the decay slope such that the VRR-indicated rate decreases more quickly during periods of paced beats.

In one embodiment, for a>1.0 and b>1.0, decreasing both a and b toward 1.0 increases VRR indicated rate during periods of sensed intrinsic activity so that the VRR indicated rate is closer to the mean intrinsic rate. Because the VRR indicated rate is closer to the mean intrinsic rate, variability in the intrinsic heart rate is more likely to trigger paces at the VRR indicated rate. On the other hand, for a>1.0 and b>1.0, increasing both a and b from 1.0 decreases the VRR indicated rate during periods of sensed intrinsic activity so that the VRR indicated rate is farther beneath the mean intrinsic rate. Because the VRR indicated rate is farther beneath the mean intrinsic rate, the same variability in the intrinsic heart rate becomes less likely to trigger paces at the VRR indicated rate.

In one embodiment, these coefficients are programmable by the user, such as by using remote programmer 125. In another embodiment, the user selects a desired performance parameter (e.g., desired degree of rate regularization, desired attack slope, desired decay slope, etc.) from a corresponding range of possible values, and device 105 automatically selects the appropriate combination of coefficients of filter 515 to provide a filter setting that corresponds to the selected user-programmed performance parameter, as illustrated generally by Table 2. Other levels of programmability or different combinations of coefficients may also be used.

TABLE 2

Example of Automatic Selection of Aspects of Filter Setting Based on a User-Programmable Performance Parameter.

| User-Programmable Performance Parameter | Intrinsic Coefficient a | Paced Coefficient b |
|---|---|---|
| 1 (Less Rate Regularization) | 2.0 | 3.0 |
| 2 | 1.8 | 2.6 |
| 3 | 1.6 | 2.2 |
| 4 | 1.4 | 1.8 |
| 5 | 1.2 | 1.4 |
| 6 (More Rate Regularization) | 1.0 | 1.0 |

Filter Rate Behavior Example 2

Figure 12:
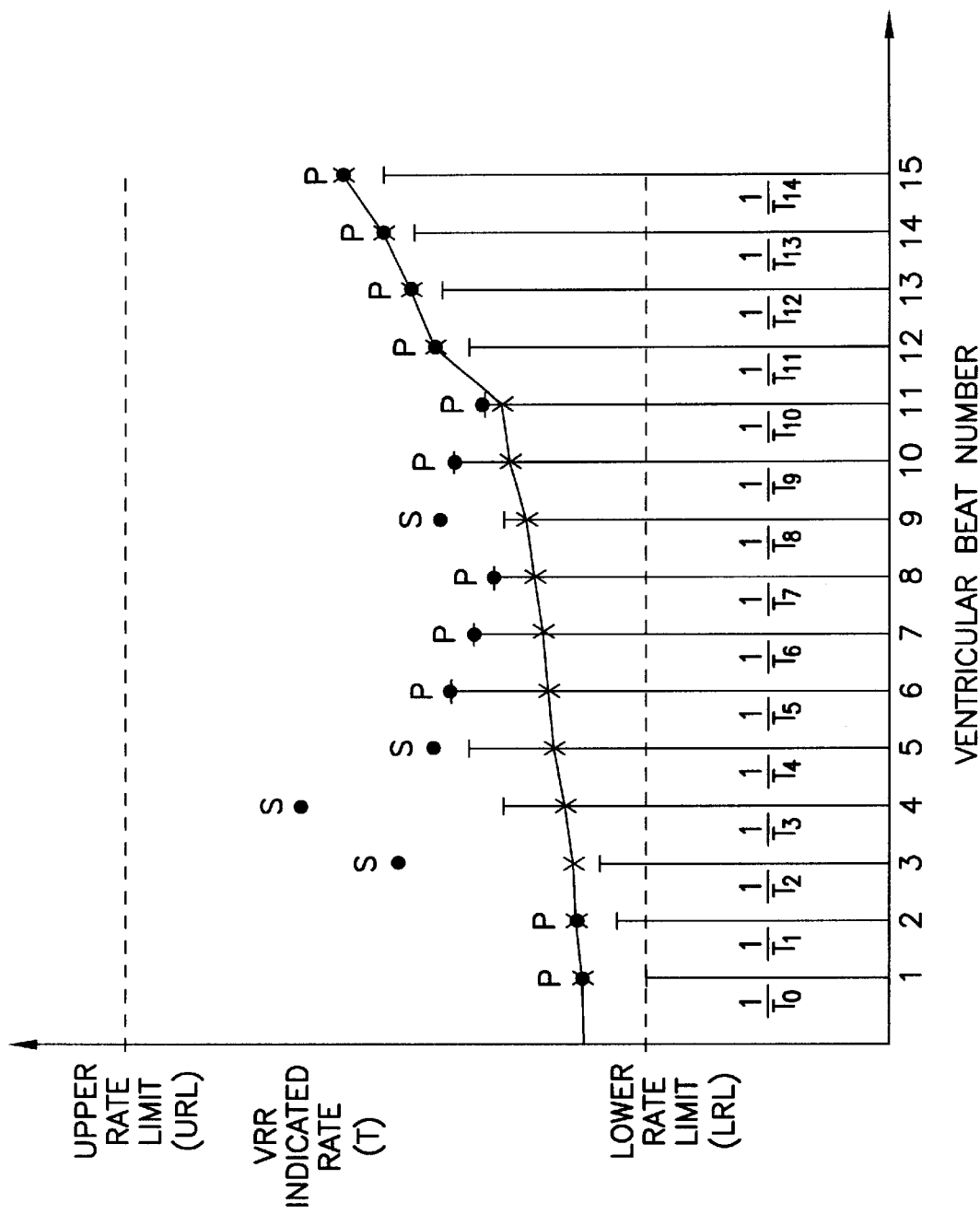
FIG. 12 is a graph illustrating generally another embodiment of operating a filter to provide the first indicated pacing rate, such as a VRR indicated rate, and delivering therapy based on the first indicated pacing rate and based on a second indicated pacing rate, such as a sensor indicated rate.

Figure 12 is a graph illustrating generally, by way of example, but not by way of limitation, one embodiment of selecting between more than one indicated pacing interval. FIG. 12 is similar to FIG. 11 in some respects, but FIG. 12 includes a second indicated pacing interval. In one embodiment, the first indicated pacing interval is the VRR indicated pacing interval, described above, and the second indicated pacing interval is a sensor indicated pacing interval, from an accelerometer, minute ventilation, or other indication of the patient's physiological need for increased cardiac output.

In one embodiment, a selected indicated pacing interval is based on the shorter of the first and second indicated pacing intervals. Stated differently, device 105 provides pacing pulses at the higher indicated pacing rate. In the example illustrated in FIG. 12, first and second beats and the twelfth through fifteenth beats are paced at the sensor indicated rate, because it is higher than the VRR indicated rate and the intrinsic rate. The third, fourth, fifth, and ninth beats are sensed intrinsic beats that are sensed during the shorter of either of the VRR and sensor indicated pacing intervals. The sixth through eighth beats and tenth and eleventh beats are paced at the VRR indicated rate, because it is higher than the sensor indicated rate. Also, for these beats, no intrinsic beats are sensed during the VRR indicated intervals. In one embodiment, the above-described equations for filter 515 operate to increase the VRR indicated rate toward the sensor-indicated rate when the sensor indicated rate is greater than the VRR indicated rate, as illustrated by first through third and twelfth through fifteenth beats in FIG. 12. In an alternate embodiment, however, $T_n = b \cdot w \cdot VV_n + (1-w) \cdot T_{n-1}$, if $VV_n$ is concluded by a VRR indicated paced beat, and $T_n = T_{n-1}$ if $VV_n$ is concluded by a sensor indicated paced beat, thereby leaving the VRR indicated rate unchanged for sensor indicated paced beats.

In this embodiment, the ranges of both the sensor indicated rate and the VRR indicated rate are limited so that they do not extend to rates higher than the URL or to rates lower than the LRL. In one embodiment, the LRL and the URL are programmable by the user, such as by using remote programmer 125.

In a further embodiment, the selected indicated pacing interval is based on the shorter of the first and second indicated pacing intervals only if an atrial tachyarrhythmia, such as atrial fibrillation, is present. Otherwise, the second indicated pacing interval is used, as described above.

Filter Rate Behavior Example 3

Figure 13:
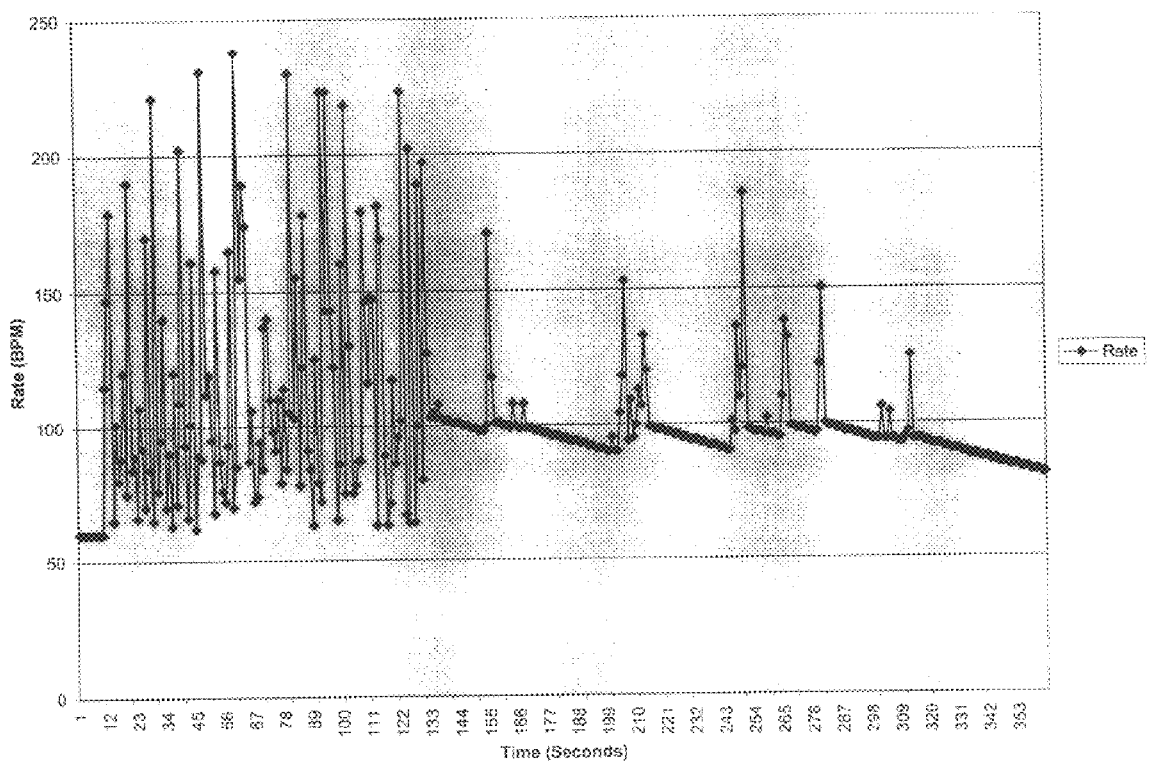
FIG. 13 is a graph illustrating generally another illustrative example of heart rate vs. time according to a VRR algorithm spreadsheet simulation.

FIG. 13 is a graph illustrating generally, by way of example, but not by way of limitation, another illustrative example of heart rate vs. time according to a spreadsheet simulation of the behavior of the above-described VRR algorithm. In FIG. 13, the VRR algorithm is turned off until time 130. Stable intrinsic lower rate behavior is modeled for times between 0 and 10 seconds. Erratic intrinsic ventricular rates, such as would result from atrial tachyarrhythmias including atrial fibrillation, are modeled during times between 10 seconds and 130 seconds. At time 130 seconds, the VRR algorithm is turned on. While some erratic intrinsic beats are subsequently observed, the VRR algorithm provides pacing that is expected to substantially stabilize the heart rate, as illustrated in FIG. 13. The VRR indicated pacing rate gradually decreases until intrinsic beats are sensed, which results in a slight increase in the VRR indicated pacing rate. Thus, the VRR algorithm favors the patient's intrinsic heart rate when it is stable, and paces at the VRR indicated heart rate when the patient's intrinsic heart rate is unstable. It is noted that FIG. 13 does not represent clinical data, but rather provides a simulation model that illustrates one example of how the VRR algorithm is expected to operate.

Filter Example 4

In one embodiment, filter 515 includes variable coefficients such as, for example, coefficients that are a function of heart rate (or its corresponding time interval). In one example, operation of the filter 515 is described by $T_n = a \cdot w \cdot VV_n + (1-w) \cdot T_{n-1}$, if $VV_n$ is concluded by an intrinsic beat, otherwise is described by $T_n = b \cdot w \cdot VV_n + (1-w) \cdot T_{n-1}$, if $VV_n$ is concluded by a paced beat, where at least one of a and b are linear, piecewise linear, or nonlinear functions of one or more previous V-V intervals such as, for example, the most recent V-V interval, $VV_n$.

Figure 14:
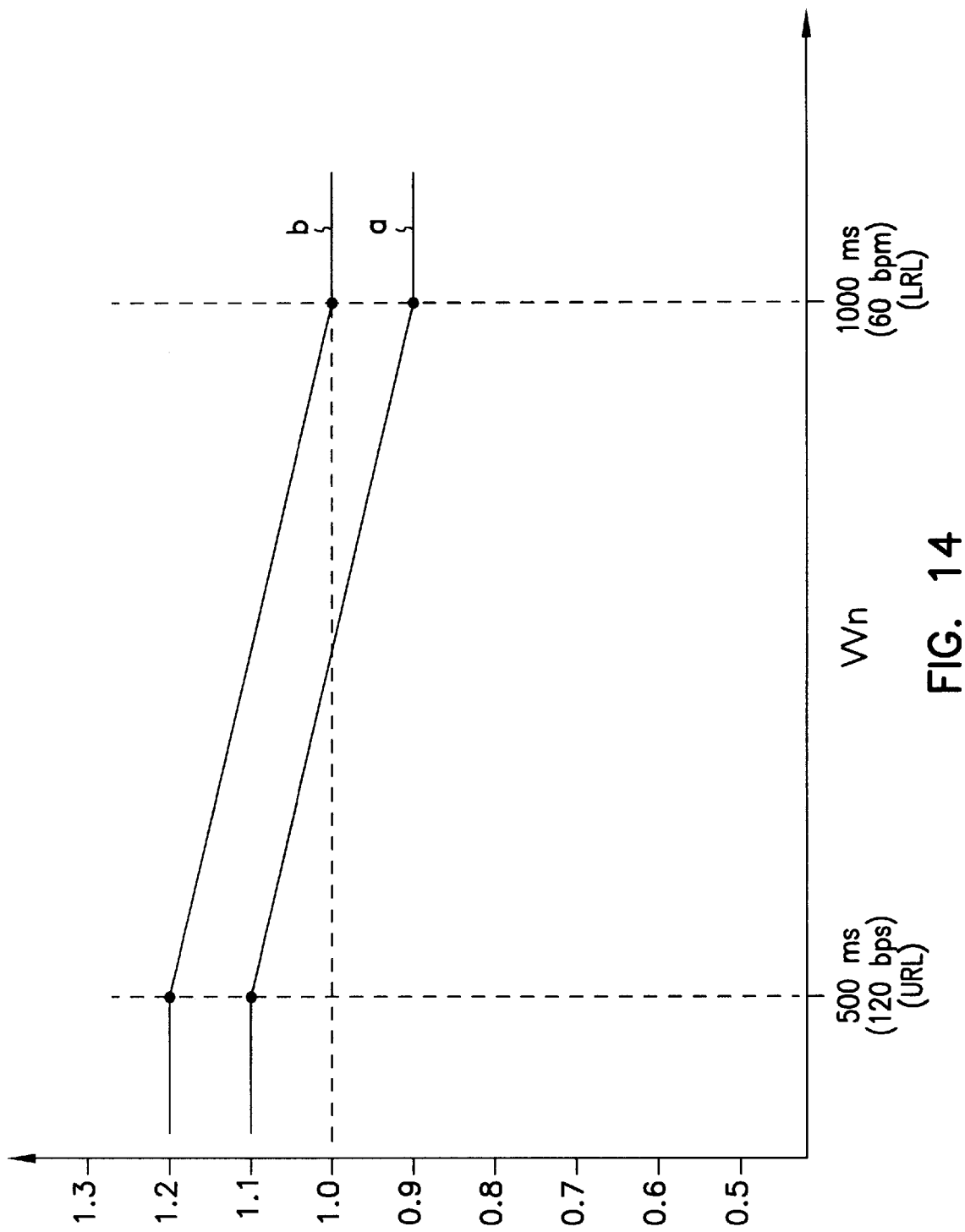
FIG. 14 is a graph illustrating generally one embodiment of using at least one of coefficients a and b as a function of heart rate (or a corresponding time interval).

FIG. 14 is a graph illustrating generally, by way of example, but not by way of limitation, one embodiment of using at least one of coefficients a and b as a function of one or more previous V-V intervals such as, for example, the most recent V-V interval, $VV_n$. In one such example, a is less than 1.0 when $VV_n$ is at or near the lower rate limit (e.g., 1000 millisecond interval or 60 beats/minute), and a is greater than 1.0 when $VV_n$ is at or near the upper rate limit (e.g., 500 millisecond interval or 120 beats/minute). For a constant b, using a smaller value of a at lower rates will increase the pacing rate more quickly for sensed events; using a larger value of a at higher rates increases the pacing rate more slowly for sensed events. In another example, b is close to 1.0 when $VV_n$ is at or near the lower rate limit, and b is greater than 1.0 when $VV_n$ is at or near the upper rate limit. For a constant a, using a smaller value of b at lower rates will decrease the pacing rate more slowly for paced events; using a larger value of b at higher rates decreases the pacing rate more quickly for paced events.

Biventricular Coordination Therapy Example

In one embodiment, the present cardiac rhythm management system utilizes the VRR filter 515 for providing biventricular pacing coordination therapy in both right and left ventricles, thereby coordinating the contractions of the right and left ventricles for more efficient pumping. The VRR filter 515 controls the timing of delivery of biventricular pacing pulses. Filter 515 provides a first indicated pacing rate that is independent of (i.e., does not track) the intrinsic atrial rate. The first indicated pacing rate is generally above the mean intrinsic ventricular rate so that it can provide substantially continuous pacing therapy. This is advantageous because, among other things, either or both of the intrinsic atrial or intrinsic ventricular heart rates may be extremely irregular, such as during atrial tachyarrhythmias. The VRR techniques described above with respect to FIGS. 1–14 promote intrinsic ventricular beats when the ventricular heart rate is substantially constant. In contrast to such Ventricular Rate Regularization that promotes intrinsic activity, biventricular coordination therapy typically uses Ventricular Rate Regulation that provides nearly continuous (i.e., to the desired degree) biventricular pacing when the ventricular rate is substantially constant. One selection of coefficients for filter 515 for obtaining nearly continuous pacing is described below.

Figure 15:
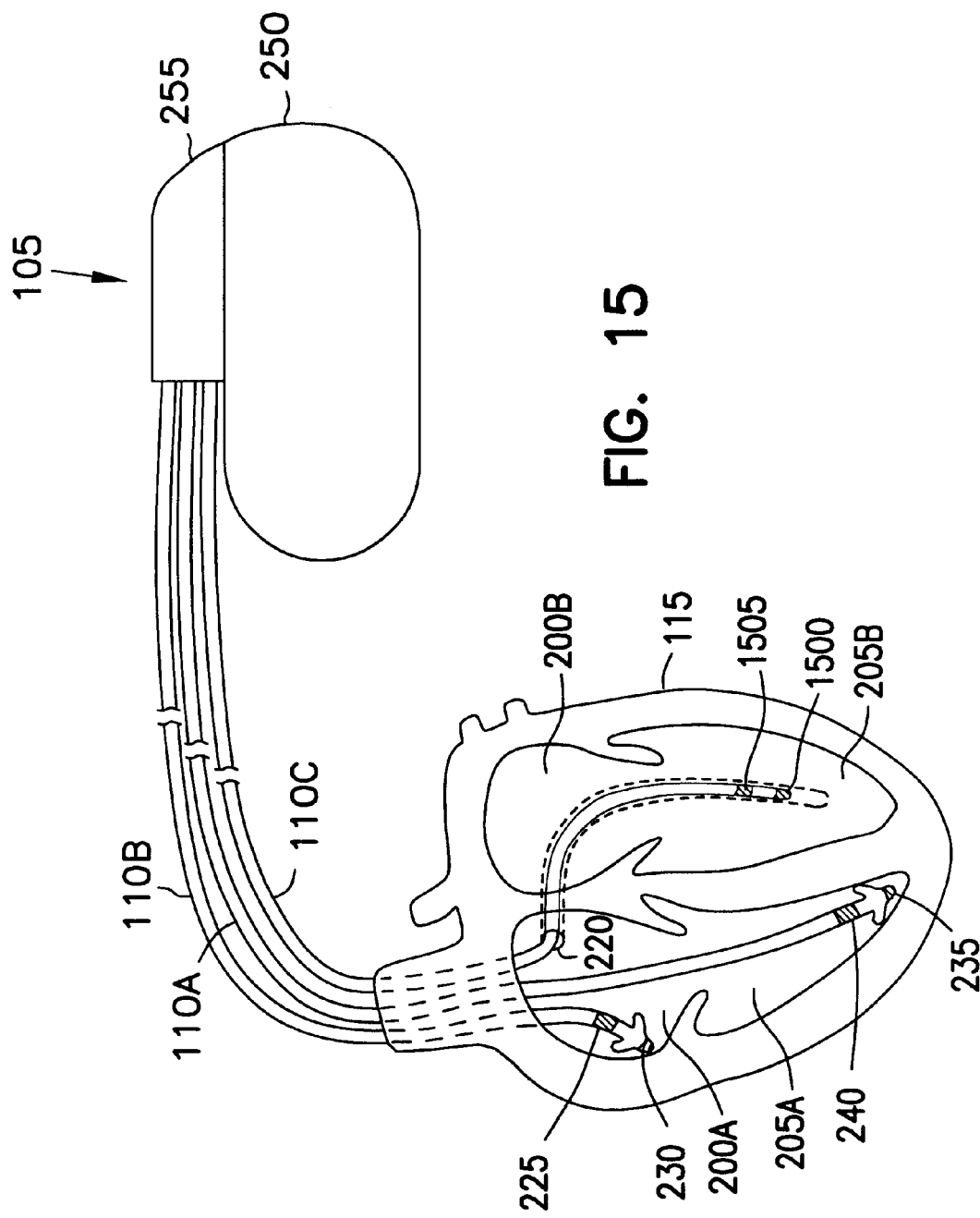
FIG. 15 is a schematic drawing, similar to FIG. 2, illustrating generally one embodiment of a cardiac rhythm management device coupled by leads to a heart, such as for providing biventricular coordination therapy.

FIG. 15 is a schematic drawing, similar to FIG. 2, illustrating generally by way of example, but not by way of limitation, one embodiment of a cardiac rhythm management device 105 coupled by leads 110A–C to a heart 115. In one such embodiment, system 100 provides biventricular coordination therapy to coordinate right ventricular and left ventricular contractions, such as for congestive heart failure patients. FIG. 15 includes a left ventricular lead 110C, inserted through coronary sinus 220 and into the great cardiac vein so that its electrodes, which include electrodes 1500 and 1505, are associated with left ventricle 205B for sensing intrinsic heart signals and providing one or more of coordination paces or defibrillation shocks.

Figure 16:
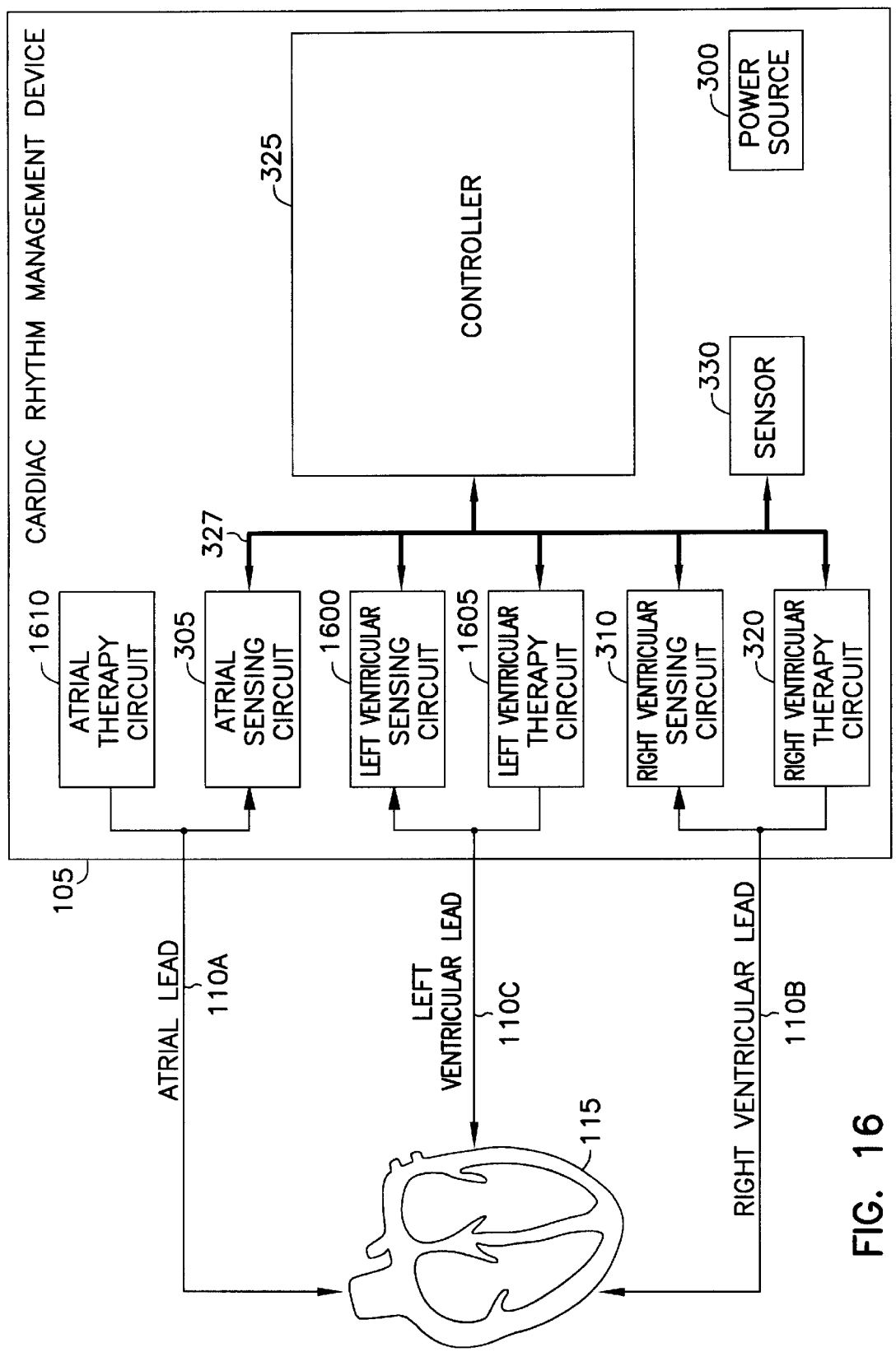
FIG. 16 is a schematic drawing, similar to FIG. 3, illustrating generally one embodiment of portions of a cardiac rhythm management device including, among other things, left ventricular sensing and therapy circuits.

FIG. 16 is a schematic drawing, similar to FIG. 3, illustrating generally by way of example, but not by way of limitation, one embodiment of portions of a cardiac rhythm management device 105, in which the left ventricular lead is coupled by lead 110C to a left ventricular sensing circuit 1600 and a left ventricular therapy circuit 1605, each of which are, in turn, coupled by node/bus 327 to controller 325. This embodiment also includes an atrial therapy circuit 1610, and a right ventricular lead 110B coupling right ventricle 205A to right ventricular sensing circuit 310 and right ventricular therapy circuit 320, each of which are, in turn, coupled by node/bus 327 to controller 325.

Figure 17:
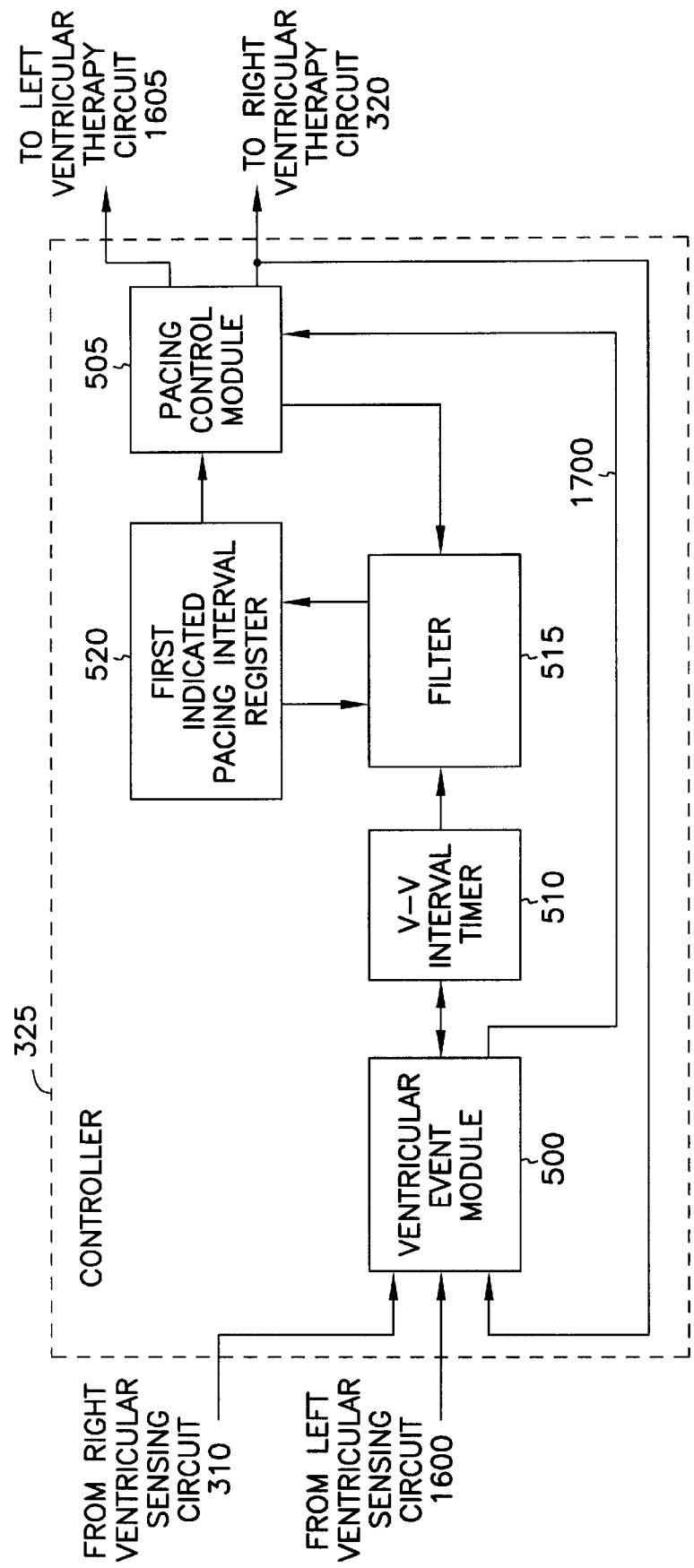
FIG. 17 is a schematic drawing, similar to FIG. 5, illustrating generally portions of one conceptual embodiment of a controller.

FIG. 17 is a schematic drawing, similar to FIG. 5, illustrating generally by way of example, but not by way of limitation, portions of one conceptual embodiment of controller 325. In this embodiment, ventricular event module 500 receives input signals from right ventricular sensing circuit 310 and left ventricular sensing circuit 1600. Pacing control module 505 provides control signals to right ventricular therapy circuit 320 and left ventricular therapy circuit 1605. Operation of filter 515 is similar to the above description accompanying FIG. 5–14, with certain differences discussed below, thereby allowing device 105 to provide biventricular coordination therapy at a VRR-indicated rate, a sensor-indicated rate, or a combination thereof.

In one embodiment, ventricular event module 500 detects sensed and paced ventricular beats from both right ventricular sensing circuit 310 and left ventricular sensing circuit 1600. An interval between successive ventricular events, referred to as a V-V interval, is recorded by a first timer, such as V-V interval timer 510. Ventricular event module 500 selects the particular ventricular events initiating and concluding the V-V interval timed by V-V interval timer 510. In a first mode of operation, the V-V interval is initiated by a right ventricular beat (paced or sensed), and the V-V interval is then concluded by the next right ventricular beat (paced or sensed). In a second mode of operation, the V-V interval is initiated by a left ventricular beat (aced or sensed), and the V-V interval is then concluded by the next left ventricular beat (paced or sensed). In a third mode of operation, the V-V interval is initiated by either a right or left ventricular beat, and the V-V interval is then concluded by the next right or left ventricular beat that occurs after expiration of a refractory period of approximately between 130 milliseconds and 500 milliseconds (e.g., 150 milliseconds). Left or right ventricular beats occurring during the refractory period are ignored. Using the refractory period ensures that the beat concluding the V-V interval is associated with a subsequent ventricular contraction, rather than a depolarization associated with the same ventricular contraction, in which the depolarization is merely sensed in the opposite ventricle from the initiating beat. Such a refractory period can also be used in conjunction with the first mode (V-V interval initiated and concluded by right ventricular beats) or the second mode (V-V interval initiated and concluded by left ventricular beats).

Filter 515 computes a "first indicated pacing interval," i.e., one indication of a desired time interval between ventricular events or, stated differently, a desired ventricular heart rate. Based on the first indicated pacing interval stored in register 520, pacing control module 505 delivers control signals to one or more of therapy circuits 320 and 340 for delivering therapy, such as biventricular pacing coordination stimuli to one or more of right ventricle 205A and left ventricle 205B, at the VRR indicated ventricular heart rate corresponding to the inverse of the duration of the first indicated pacing interval.

Ventricular event module 500 also includes an output node/bus 1700 coupled to pacing control module 505. Ventricular event module 500 communicates to pacing control module 505 information about the occurrence (e.g., timing, origin, etc.) of right and left ventricular sensed beats, so that pacing control module 505 can issue biventricular coordination therapy to obtain coordinated right and left ventricular contractions. In one embodiment, a sensed right ventricular contraction triggers an immediate or very slightly delayed left ventricular pacing pulse, either alone, or in conjunction with a right ventricular pacing pulse. Similarly, a sensed left ventricular contraction triggers an immediate or very slightly delayed right ventricular pacing pulse, either alone or in conjunction with a left ventricular pacing pulse. This ensures that contractions of the right and left ventricles are coordinated to provide more efficient pumping of blood by the heart 115. In one embodiment, the controller illustrated in FIG. 17 includes a sensor channel, as discussed above with respect to FIG. 9. In this embodiment, device 105 provides biventricular coordination therapy at a VRR-indicated rate, a sensor-indicated rate, or a combination thereof.

In one embodiment, the coefficients of filter 515 are programmable by the user, such as by using remote programmer 125, as described above, in order to obtain a desired degree of pacing vs. sensing. In another embodiment, the user selects a desired performance parameter (e.g., desired degree of pacing vs. sensing, etc.) from a corresponding range of possible values, and device 105 automatically selects the appropriate combination of coefficients of filter 515 to provide a filter setting that corresponds to the selected user-programmed performance parameter, as illustrated generally by Table 3. Other levels of programmability or different combinations of coefficients may also be used.

TABLE 3

Example of Automatic Selection of Aspects of Filter Setting Based on a User-Programmable Performance Parameter Such as For Providing Biventricular Coordination Therapy.

| User-Programmable Performance Parameter | Intrinsic Coefficient a | Paced Coefficient b |
|---|---|---|
| 1 (More Pacing) | 0.6 | 1.05 |
| 2 | 0.7 | 1.2 |
| 3 | 0.8 | 1.3 |
| 4 | 0.9 | 1.4 |
| 5 (Less Pacing) | 1.0 | 1.5 |

In a further embodiment, device 105 uses a mapping, such as illustrated in Table 3, in a feedback control loop to automatically select the "performance parameter" of Table 3 and corresponding coefficients. The user programs a mean pacing frequency goal. Device 105 measures the mean pacing frequency over a predetermined period of time or predetermined number of V-V intervals. The measured mean pacing is compared to the mean pacing frequency goal. If the measured mean pacing frequency is higher than the goal mean pacing frequency, the performance parameter in Table 3 is incremented/decremented toward less pacing. Conversely, if the measured mean pacing frequency is lower than the goal mean pacing frequency, the performance parameter in Table 3 is incremented/decremented toward more pacing. In a further embodiment, the measured mean pacing frequency is compared to values that are slightly offset about the goal mean pacing frequency (e.g., goal mean pacing frequency $+/-\Delta$) to provide a band of acceptable measured mean pacing frequencies within which the performance parameter is not switched.

Av Delay Regulation Embodiment For Congestive Heart Failure Patients

The preceding embodiment illustrated techniques of providing rate regulation for delivering biventricular coordination therapy to congestive heart failure patients. Such techniques are particularly advantageous in the presence of atrial tachyarrhymias, such as atrial fibrillation. When atrial tachyarrhythmias are present, atrial rate tracking would result in too-fast and irregular biventricular coordination therapy. Because atrial tachyarrhythmias often induce irregular ventricular cardiac cycle lengths, ventricular tracking would also produce erratic results if the above-described VRR techniques are not used.

Where no atrial tachyarrhythmias are present, however, biventricular coordination therapy based on atrial rate tracking is possible. The above-disclosed techniques are still useful, however, for providing a first indicated timing interval. In one example, the first indicated timing interval is a filter indicated atrioventricular (AV) delay based on the intrinsic AV delay, i.e., the interval between a sensed P wave and a successively sensed R wave. In this example, biventricular coordination therapy is provided based on the tracking of an atrial rate. Each biventricular coordination pacing pulse is delivered after the filter indicated AV delay. The filter indicated AV delay is computed similarly to the VRR techniques described above, with certain differences described more particularly below.

Figure 18:
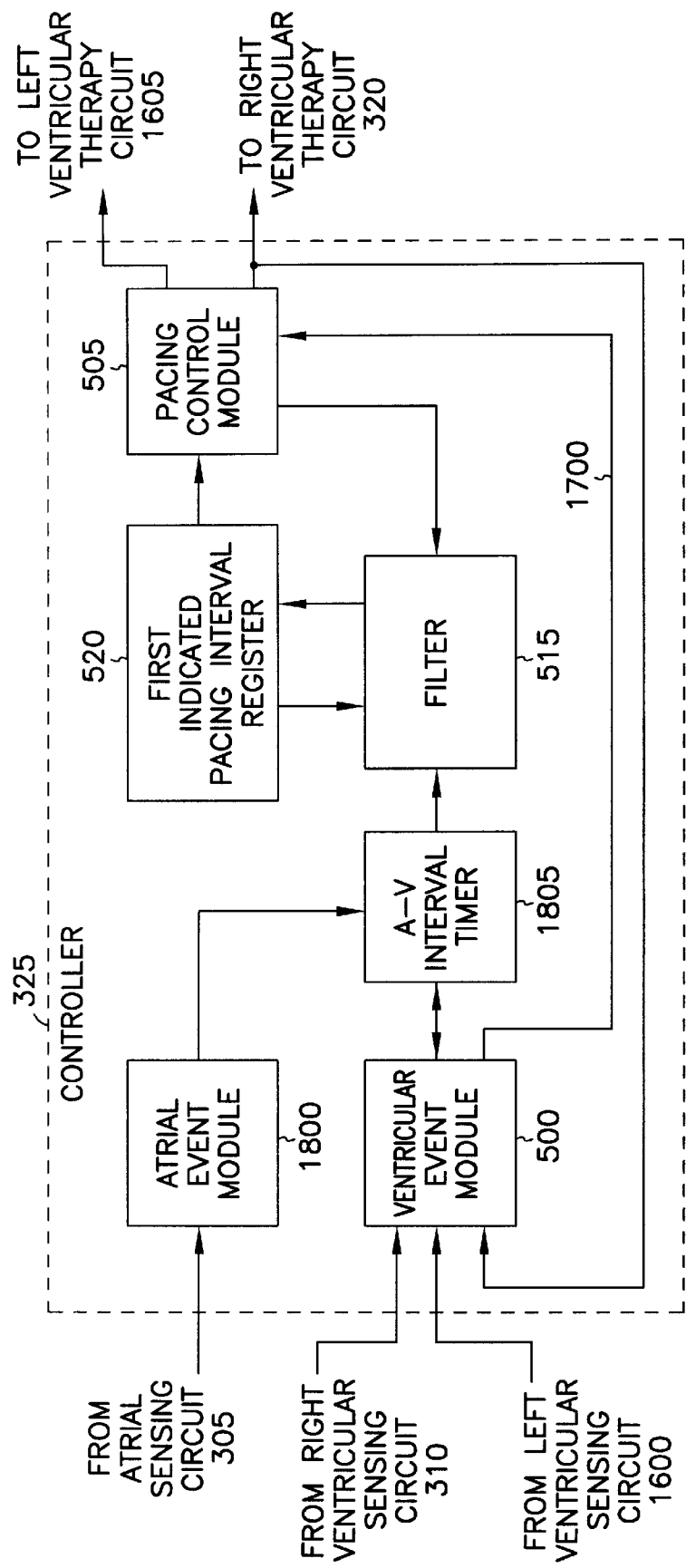
FIG. 18 is a schematic diagram, similar to FIG. 17, illustrating generally another conceptualization of portions of a controller used for regulating an AV interval based on a filter indicated AV delay.

FIG. 18 is a schematic diagram, similar to FIG. 17, illustrating generally by way of example, but not by way of limitation, another conceptualization of portions of controller 325 used for regulating the AV interval based on a filter indicated AV delay. In FIG. 18, atrial event module 1800 and ventricular event module 500 provide information about paced or sensed atrial events and paced or sensed ventricular events, respectively, to AV interval timer 1805. AV interval timer 1805 times an AV interval initiated by an atrial event, and concluded by a ventricular event, such as described above with respect to FIG. 17.

In one example, operation of the filter 515 is described by $T_n = a \cdot w \cdot AV_n + (1-w) \cdot T_{n-1}$, if $AV_n$ is concluded by an intrinsic beat, otherwise is described by $T_n = b \cdot w \cdot AV_n + (1-w) \cdot T_{n-1}$, if $AV_n$ is concluded by a paced beat, where $T_n$ is the newly computed value of the filter indicated AV interval, $T_{n-1}$ is the previous value of the filter indicated AV interval, $AV_n$ is the time interval corresponding to the most recent AV delay period, and a, b, and w are coefficients. In one embodiment, weighting coefficient w, intrinsic coefficient a, and paced coefficient b, are variables. Different selections of w, a, and b, will result in different operation of the present method and apparatus. For example, as w increases the weighting effect of the most recent A-V interval $AV_n$ increases and the weighting effect of the previous first indicated pacing rate $T_{n-1}$ decreases. In one embodiment, $w=\frac{1}{16}=0.0625$. In another embodiment, $w=\frac{1}{32}$. Another possible range for w is from $w=\frac{1}{2}$ to $w=\frac{1}{1024}$. A further possible range for w is from $w\approx0$ to $w\approx1$. Other values of w, which need not include division by powers of two, may be substituted without departing from the present method and apparatus.

In one embodiment, intrinsic coefficient a, is selected to be less than (or, alternatively, less than or equal to) 1.0. In one example, the intrinsic coefficient a is selected to be lesser in value than the pacing coefficient b. In one embodiment, $a\approx0.6$ and $b\approx1.5$. In another embodiment, $a=1.0$ and $b=1.05$. One possible range for a is from $a=0.6$ to $a=1.0$, and for b is from $b=1.05$ to $b=1.5$. The coefficients may vary without departing from the present method and apparatus.

In one embodiment, these coefficients are programmable by the user, such as by using remote programmer 125. In another embodiment, the user selects a desired performance parameter (e.g., desired degree pacing vs. sensing, desired attack slope, desired decay slope, etc.) from a corresponding range of possible values, and device 105 automatically selects the appropriate combination of coefficients of filter 515 to provide a filter setting that corresponds to the selected user-programmed performance parameter, as illustrated generally by Table 4. Other levels of programmability or different combinations of coefficients may also be used.

TABLE 4

Example of Automatic Selection of Aspects of Filter Setting Based on a User-Programmable Performance Parameter, Such as for AV Delay Regulation

| User-Programmable Performance Parameter | Intrinsic Coefficient a | Paced Coefficient b |
|---|---|---|
| 1 (Less Aggressive Attack/Decay) | 1.0 | 1.05 |
| 2 | 0.9 | 1.2 |
| 3 | 0.8 | 1.3 |
| 4 | 0.7 | 1.4 |
| 5 (More Aggressive Attack/Decay) | 0.6 | 1.5 |

In a further embodiment, device 105 uses a mapping, such as illustrated in Table 4, in a feedback control loop to automatically select the "performance parameter" and corresponding coefficients. The user programs a mean sense frequency goal. Device 105 measures the mean frequency of sensed ventricular events ("measured mean sense frequency") over a predetermined period of time or predetermined number of A-V intervals, and adjusts the performance parameter and corresponding coefficients to direct the measured mean sense frequency toward the mean sense frequency goal.

The above techniques provide an example in which AV delay is regulated. However, it is understood that these techniques extend to the regulation of any other timing interval. In one embodiment, for example, operation of filter 515 is expressed more generically as $T_n=A \cdot EE_n+B \cdot T_{n-1}$, if $EE_n$ is concluded by an intrinsic beat, otherwise is described by $T_n=C \cdot EE_n+D \cdot T_{n-1}$, if $EE_n$ is concluded by a paced beat, where $T_n$ is the newly computed value of the indicated timing interval, $T_{n-1}$ is the previous value of the indicated timing interval, $EE_n$ is the measured timing interval between any two events, and A, B, C, and D are coefficients.

CONCLUSION

The above-described system provides, among other things, a cardiac rhythm management system including techniques for computing an indicated pacing interval, AV delay, or other timing interval. In one embodiment, a variable indicated pacing interval is computed based at least in part on an underlying intrinsic heart rate. The indicated pacing interval is used to time the delivery of biventricular coordination therapy even when ventricular heart rates are irregular, such as in the presence of atrial fibrillation. In another embodiment, a variable filter indicated AV interval is computed based at least in part on an underlying intrinsic AV interval. The indicated AV interval is used to time the delivery of atrial tracking biventricular coordination therapy when atrial heart rhythms are not arrhythmic. Other indicated timing intervals may be similarly determined. The indicated pacing interval, AV delay, or other timing interval can also be used in combination with a sensor indicated rate indicator.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method, comprising:
   obtaining actual timing intervals between cardiac events;
   computing a first indicated timing interval based at least on a most recent actual timing interval duration and a previous value of the first indicated timing interval, including weighting at least one of (1) the most recent actual timing interval duration, or (2) the previous value of the first indicated timing interval, based on whether the most-recent actual timing interval is concluded by a paced beat or a sensed beat; and
   providing pacing therapy, based on the first indicated timing interval.

2. The method of claim 1, in which computing the first indicated timing interval includes summing a first addend based on the most recent actual timing interval duration and a second addend based on the previous value of the first indicated timing interval, wherein at least one of the first and second addends is different if the most recent actual timing interval is concluded by an intrinsic beat than if the most recent actual timing interval is concluded by a paced beat.

3. The method of claim 1, in which computing the first indicated timing interval ($T_n$) is carried out according to $T_n=A \cdot EE_n+B \cdot T_{n-1}$ where A and B are coefficients, $EE_n$ is the most recent actual timing interval between events, and $T_{n-1}$ is the previous value of the first indicated timing interval.

4. The method of claim 3, in which computing the first indicated timing interval ($T_n$) is carried out according to: $T_n=A \cdot EE_n+B \cdot T_{n-1}$ if $EE_n$ is concluded by an intrinsic beat, otherwise is carried out according to $T_n=C \cdot EE_n+D \cdot T_{n-1}$, if $EE_n$ is concluded by a paced beat, where C and D are coefficients.

5. The method of claim 4, in which at least one of A, B, C, and D is a function of heart rate.

6. The method of claim 1, in which computing the first indicated timing interval ($T_n$) is carried out according to $T_n=a \cdot w \cdot EE_n+(1-w) \cdot T_{n-1}$ if $EE_n$ is concluded by an intrinsic beat, otherwise is carried out according to $T_n=b \cdot w \cdot EE_n+(1-w) \cdot T_{n-1}$, if $EE_n$ is concluded by a paced beat, where a, b, and w are coefficients, $EE_n$ is the most recent actual timing interval duration, and $T_{n-1}$ is the previous value of the first indicated timing interval.

7. The method of claim 6, in which a is approximately between 1.0 and 2.0, b is approximately between 1.0 and 3.0, and w is approximately between 0 and 1.

8. The method of claim 1, in which providing pacing therapy is also based on a second indicated timing interval that is based on a sensor.

9. The method of claim 1, in which the first indicated timing interval is limited by at least one of a maximum value and a minimum interval value.

10. The method of claim 1, in which providing pacing therapy is based on the first indicated timing interval if atrial tachyarrhythmia is present, and providing pacing therapy is independent of the first indicated timing interval if no atrial tachyarrhythmia is present.

11. The method of claim 1, further including providing to a first ventricle a pace pulse triggered by a sensed beat in a second ventricle different from the first ventricle.

12. A method comprising:
    obtaining actual timing intervals between cardiac events;
    computing a first indicated timing interval based at least on a most recent actual timing interval duration and a previous value of the first indicated timing interval; and
    providing pacing therapy, based on the first indicated timing interval, in which computing the first indicated timing interval is also based on a remotely user-programmable parameter that corresponds to a desired degree of paced beats vs. sensed beats.

13. The method of claim 12, in which computing the first indicated timing interval includes summing a first addend based on the most recent actual timing interval duration and a second addend based on the previous value of the first indicated timing interval, wherein at least one of the first and second addends is different if the most recent actual timing interval is concluded by an intrinsic beat than if the most recent actual timing interval is concluded by a paced beat.

14. The method of claim 12, in which computing the first indicated timing interval ($T_n$) is carried out according to $T_n=A \cdot EE_n+B \cdot T_{n-1}$ where A and B are coefficients, $EE_n$ is the most recent actual timing interval between events, and $T_{n-1}$ is the previous value of the first indicated timing interval.

15. The method of claim 14, in which computing the first indicated timing interval ($T_n$) is carried out according to: $T_n=A \cdot EE_n+B \cdot T_{n-1}$ if $EE_n$ is concluded by an intrinsic beat, otherwise is carried out according to $T_n=C \cdot EE_n+D \cdot T_{n-1}$, if $EE_n$ is concluded by a paced beat, where C and D are coefficients.

16. The method of claim 15, in which at least one of A, B, C, and D is a function of heart rate.

17. The method of claim 12, in which computing the first indicated timing interval ($T_n$) is carried out according to $T_n = a \cdot w \cdot EE_n + (1-w) \cdot T_{n-1}$ if $EE_n$ is concluded by an intrinsic beat, otherwise is carried out according to $T_n = b \cdot w \cdot EE_n + (1-w) \cdot T_{n-1}$, if $EE_n$ is concluded by a paced beat, where a, b, and w are coefficients, $EE_n$ is the most recent actual timing interval duration, and $T_{n-1}$ is the previous value of the first indicated timing interval.

18. The method of claim 17, in which a is approximately between 1.0 and 2.0, b is approximately between 1.0 and 3.0, and w is approximately between 0 and 1.

19. The method of claim 12, in which providing pacing therapy is also based on a second indicated timing interval that is based on a sensor.

20. The method of claim 12, in which the first indicated timing interval is limited by at least one of a maximum value and a minimum interval value.

21. The method of claim 12, in which providing pacing therapy is based on the first indicated timing interval if atrial tachyarrhythmia is present, and providing pacing therapy is independent of the first indicated timing interval if no atrial tachyarrhythmia is present.

22. A method comprising:
obtaining actual timing intervals between cardiac events;
computing a first indicated timing interval based at least on a most recent actual timing interval duration and a previous value of the first indicated timing interval; and
providing pacing therapy, based on the first indicated timing interval, in which computing the first indicated timing interval is also based on a goal proportion of paced beats to sensed beats.

23. The method of claim 22, in which computing the first indicated timing interval includes summing a first addend based on the most recent actual timing interval duration and a second addend based on the previous value of the first indicated timing interval, wherein at least one of the first and second addends is different if the most recent actual timing interval is concluded by an intrinsic beat than if the most recent actual timing interval is concluded by a paced beat.

24. The method of claim 22, in which computing the first indicated timing interval ($T_n$) is carried out according to $T_n = A \cdot EE_n + B \cdot T_{n-1}$ where A and B are coefficients, $EE_n$ is the most recent actual timing interval between events, and $T_{n-1}$ is the previous value of the first indicated timing interval.

25. The method of claim 24, in which computing the first indicated timing interval ($T_n$) is carried out according to: $T_n = A \cdot EE_n + B \cdot T_{n-1}$ if $EE_n$ is concluded by an intrinsic beat, otherwise is carried out according to $T_n = C \cdot EE_n + D \cdot T_{n-1}$, if $EE_n$ is concluded by a paced beat, where C and D are coefficients.

26. The method of claim 24, in which at least one of A, B, C, and D is a function of heart rate.

27. The method of claim 22, in which computing the first indicated timing interval ($T_n$) is carried out according to $T_n = a \cdot w \cdot EE_n + (1-w) \cdot T_{n-1}$ if $EE_n$ is concluded by an intrinsic beat, otherwise is carried out according to $T_n = b \cdot w \cdot EE_n + (1-w) \cdot T_{n-1}$, if $EE_n$ is concluded by a paced beat, where a, b, and w are coefficients, $EE_n$ is the most recent actual timing interval duration, and $T_{n-1}$ is the previous value of the first indicated timing interval.

28. The method of claim 27, in which a is approximately between 1.0 and 2.0, b is approximately between 1.0 and 3.0, and w is approximately between 0 and 1.

29. The method of claim 22, in which providing pacing therapy is also based on a second indicated timing interval that is based on a sensor.

30. The method of claim 22, in which the first indicated timing interval is limited by at least one of a maximum value and a minimum interval value.

31. The method of claim 22, in which providing pacing therapy is based on the first indicated timing interval if atrial tachyarrhythmia is present, and providing pacing therapy is independent of the first indicated timing intreval if no atrial tachyarrhythmia is present.

32. A method, comprising:
obtaining V-V intervals between ventricular beats;
computing a first indicated pacing interval based at least on a most recent V-V interval duration and a previous value of the first indicated pacing interval; and
providing pacing therapy to first and second ventricles, based on the first indicated pacing interval.

33. The method of claim 32, in which obtaining V-V intervals between ventricular beats includes obtaining the V-V intervals between ventricular beats of the same ventricle.

34. The method of claim 32, in which obtaining V-V intervals between ventricular beats includes obtaining the V-V intervals between ventricular beats of different ventricles.

35. The method of claim 32, in which obtaining V-V intervals between ventricular beats includes:
obtaining an initiating ventricular beat, in one of the first and second ventricles, the initiating ventricular beat initiating a V-V interval; and
obtaining a concluding ventricular beat, in one of the first and second ventricles, the concluding ventricular beat being the next ventricular beat detected after expiration of a first time delay, and the concluding ventricular beat concluding the V-V interval.

36. The method of claim 32, in which computing the first indicated pacing interval includes differently weighting at least one of (1) the most recent V-V interval duration, or (2) the previous value of the first indicated pacing interval, if the most-recent V-V interval is concluded by a paced beat than if the most recent V-V interval is concluded by a sensed beat.

37. The method of claim 32, in which computing the first indicated pacing interval includes summing a first addend based on the most recent V-V interval duration and a second addend based on the previous value of the first indicated pacing interval, wherein at least one of the first and second addends is different if the most recent V-V interval is concluded by an intrinsic beat than if the most recent V-V interval is concluded by a paced beat.

38. The method of claim 32, in which computing the first indicated pacing interval ($T_n$) is carried out according to $T_n = A \cdot VV_n + B \cdot T_{n-1}$, where A and B are coefficients, $VV_n$ is the most recent V-V interval duration, and $T_{n-1}$ is the previous value of the first indicated pacing interval.

39. The method of claim 38, in which computing the first indicated pacing interval ($T_n$) is carried out according to: $T_n = A \cdot VV_n + B \cdot T_{n-1}$, if $VV_n$ is concluded by an intrinsic beat, otherwise is carried out according to $T_n = C \cdot VV_n + D \cdot T_{n-1}$, if $VV_n$ is concluded by a paced beat, where C and D are coefficients.

40. The method of claim 39, in which at least one of A, B, C, and D is a function of heart rate.

41. The method of claim 32, in which computing the first indicated pacing interval ($T_n$) is carried out according to $T_n = a \cdot w \cdot VV_n + (1-w) \cdot T_{n-1}$ if $VV_n$ is concluded by an intrinsic beat, otherwise is carried out according to $T_n = b \cdot w \cdot VV_n + (1-w) \cdot T_{n-1}$, if $VV_n$ is concluded by a paced beat, where a, b, and w are coefficients, $VV_n$ is the most recent V-V interval duration, and $T_{n-1}$ is the previous value of the first indicated pacing interval.

42. The method of claim 32, in which providing pacing therapy is also based on a second indicated pacing interval that is based on a sensor.

43. The method of claim 32, in which providing pacing therapy is based on the first indicated pacing interval, if an atrial tachyarrhythmia is present, and providing pacing therapy is independent of the first indicated pacing interval if no atrial tachyarrhythmia is present.

44. The method of claim 43, in which the atrial tachyarrhythmia is atrial fibrillation.

45. The method of claim 32, in which providing pacing therapy is based on the first indicated pacing interval if the first indicated pacing interval is longer than a first predetermined value, and providing pacing therapy is independent of the first indicated pacing interval if the first indicated pacing interval is shorter than the first predetermined value.

46. The method of claim 32, in which computing the first indicated pacing interval is also based on a remotely user-programmable parameter that corresponds to a desired degree of paced ventricular beats vs. sensed ventricular beats.

47. The method of claim 32, in which computing the first indicated pacing interval is also based on a goal proportion of paced ventricular beats to sensed ventricular beats.

48. The method of claim 32, in which the first indicated pacing interval is limited by at least one of a maximum interval value and a minimum interval value.

49. A cardiac rhythm management system, comprising:
a sensing circuit for sensing events;
a controller, obtaining timing intervals between events and computing a first indicated timing interval based at least on a most recent actual timing interval duration and a previous value of the first indicated timing interval;
a filter that computes the first indicated timing interval by weighting at least one of (1) the most recent timing interval duration, or (2) the previous value of the first indicated timing interval, based on whether the most recent actual timing interval is concluded by a paced beat or a sensed beat; and
a therapy circuit, providing pacing therapy based on the first indicated timing interval.

50. The system of claim 49, in which the filter includes coefficients A, B, C, and D, and the filter computes the first indicated timing interval ($T_n$) according to: $T_n = A \cdot EE_n + B \cdot T_{n-1}$ if $EE_n$ is concluded by an intrinsic beat, otherwise is carried out according to $T_n = C \cdot EE_n + D \cdot T_{n-1}$, if $EE_n$ is concluded by a paced beat, where $EE_n$ is the most recent actual timing interval duration and $T_{n-1}$ is the previous value of the first indicated timing interval.

51. The system of claim 49, further including a sensor, and in which the controller computes a second indicated timing interval based on signals received from the sensor, and in which the therapy circuit provides pacing therapy that is also based on the second indicated timing interval.

52. The system of claim 51, further including a selection module, selecting between the first and second indicated timing intervals to provide a selected timing interval.

53. The system of claim 49, including a programmer remote from and communicatively coupled to the controller, and in which the controller includes a first parameter that is programmable by the programmer, and the programmer includes an indicator based on a second parameter received from the controller.

54. A cardiac rhythm management system, comprising:
a sensing circuit for sensing events;
a controller, obtaining timing intervals between events and computing a first indicated timing interval based at least on a most recent actual timing interval duration and a previous value of the first indicated timing interval, and in which the first indicated timing interval is also based on a first parameter that corresponds to a desired proportion of paced ventricular beats to sensed ventricular beats; and
a therapy circuit, providing pacing therapy based on the first indicated timing interval.

55. The system of claim 54, in which the filter includes coefficients A, B, C, and D, and the filter computes the first indicated timing interval ($T_n$) according to: $T_n = A \cdot EE_n + B \cdot T_{n-1}$ if $EE_n$ is concluded by an intrinsic beat, otherwise is carried out according to $T_n = C \cdot EE_n + D \cdot T_{n-1}$, if $EE_n$ is concluded by a paced beat, where $EE_n$ is the most recent actual timing interval duration and $T_{n-1}$ is the previous value of the first indicated timing interval.

56. The system of claim 54, further including a sensor, and in which the controller computes a second indicated timing interval based on signals received from the sensor, and in which the therapy circuit provides pacing therapy that is also based on the second indicated timing interval.

57. The system of claim 56, further including a selection module, selecting between the first and second indicated timing intervals to provide a selected timing interval.

58. A cardiac rhythm management system, comprising:
a sensing circuit for sensing events;
a controller, obtaining timing intervals between events and computing a first indicated timing interval based at least on a most recent actual timing interval duration and a previous value of the first indicated timing interval, and in which the controller includes a goal proportion of paced ventricular beats to sensed ventricular beats, and the first indicated timing interval is also based on the goal; and
a therapy circuit, providing pacing therapy based on the first indicated timing interval.

59. The system of claim 58, in which the filter includes coefficients A, B, C, and D, and the filter computes the first indicated timing interval ($T_n$) according to: $T_n = A \cdot EE_n + B \cdot T_{n-1}$ if $EE_n$ is concluded by an intrinsic beat, otherwise is carried out according to $T_n = C \cdot EE_n + D \cdot T_{n-1}$, if $EE_n$ is concluded by a paced beat, where $EE_n$ is the most recent actual timing interval duration and $T_{n-1}$ is the previous value of the first indicated timing interval.

60. The system of claim 58, further including a sensor, and in which the controller computes a second indicated timing interval based on signals received from the sensor, and in which the therapy circuit provides pacing therapy that is also based on the second indicated timing interval.

61. The system of claim 60, further including a selection module, selecting between the first and second indicated timing intervals to provide a selected timing interval.

62. A cardiac rhythm management system, comprising:
at least one ventricular sensing circuit;
a controller, the controller including:
an V-V interval timer, obtaining V-V intervals between successive events in at least one ventricle;
a first register, for storing a first indicated pacing interval; and
a filter, updating the first indicated pacing interval based on a most recent V-V interval provided by the VV interval timer and previous value of the first indicated pacing interval stored the first register; and
a ventricular therapy circuit, providing pacing therapy to first and second ventricles based at least partially on the first indicated pacing interval.

63. The system of claim 62, in which the filter differently weighting at least one of (1) the most recent VV interval duration, or (2) the previous value of the first indicated pacing interval, if the most recent AV interval is concluded by a paced beat than if the most recent AV interval is concluded by a sensed beat.

64. The system of claim 63, in which the filter includes coefficients A, B, C, and D, and the filter computes the first indicated pacing interval ($T_n$) according to: $T_n = A \cdot VV_n + B \cdot T_{n-1}$ if $VV_n$ is concluded by an intrinsic beat, otherwise is carried out according to $T_n = C \cdot VV_n + D \cdot T_{n-1}$, if $VV_n$ is concluded by a paced beat, where $VV_n$ is the most recent VV interval duration and $T_{n-1}$ is the previous value of the first indicated pacing interval.

65. The system of claim 62, further including a sensor, and in which the controller computes a second indicated pacing interval based on signals received from the sensor, and in which the therapy circuit provides pacing therapy that is also based on the second indicated pacing interval.

66. The system of claim 62, further including an atrial sensing circuit, and in which the filter includes a switch that enables the filter when the atrial sensing circuit indicates that an atrial tachyarrhythmia is present.

67. The system of claim 62, including a programmer remote from and communicatively coupled to the controller, and in which the controller includes a first parameter that is programmable by the programmer, and the programmer includes an indicator based on a second parameter received from the controller.

68. The system of claim 67, in which the first indicated pacing interval is also based on the remotely user-programmable first parameter, wherein the first parameter corresponds to a desired degree of paced ventricular beats vs. sensed ventricular beats.

69. The system of claim 62, in which the controller includes a goal proportion of paced ventricular beats to sensed ventricular beats, and the first indicated pacing interval is also based on the goal.

70. The system of claim 62, further including a first electrode associated with the first ventricle and a second electrode associated with the second ventricle.

71. The system of claim 62, in which the first indicated pacing interval is limited by at least one of a maximum interval value and a minimum interval value.

* * * * *

UNITED STATES PATENT AND TRADEMARK OFFICE
CERTIFICATE OF CORRECTION

PATENT NO. : 6,285,907 B1  Page 1 of 1
DATED : September 4, 2001
INVENTOR(S) : Andrew P. Kramer, Jeffrey E. Stahmann, Rene H. Wentkowski, Kenneth L. Baker, Jesse W. Hartley and David B. Krig It is certified that error appears in the above-identified patent and that said Letters Patent is hereby corrected as shown below:

Column 24,
Line 61, insert a space between "($T_n$)" and "is".

Column 25,
Line 49, delete referenced claim No. "24" and insert -- 25 --, therefor.

Column 28,
Line 62, insert -- in -- between "stored" and "the".

Signed and Sealed this

Fourteenth Day of May, 2002

Attest:

JAMES E. ROGAN
*Attesting Officer*       *Director of the United States Patent and Trademark Office*